US009414750B2

(12) United States Patent
Lovely

(10) Patent No.: US 9,414,750 B2
(45) Date of Patent: *Aug. 16, 2016

(54) INFRARED DENTAL IMAGING

(71) Applicant: LuxRay Dental Systems, Inc., Portland, OR (US)

(72) Inventor: Peter S. Lovely, Portland, OR (US)

(73) Assignee: LuxRay Dental Systems, Inc., Portland, OR (US)

( * ) Notice: Subject to any disclaimer, the term of this patent is extended or adjusted under 35 U.S.C. 154(b) by 10 days.

This patent is subject to a terminal disclaimer.

(21) Appl. No.: 14/032,127

(22) Filed: Sep. 19, 2013

(65) Prior Publication Data

US 2014/0186791 A1    Jul. 3, 2014

Related U.S. Application Data

(63) Continuation of application No. 11/636,177, filed on Dec. 8, 2006, now Pat. No. 8,556,625.

(60) Provisional application No. 60/748,809, filed on Dec. 8, 2005.

(51) Int. Cl.
*A61C 3/00* (2006.01)
*A61B 5/00* (2006.01)
(Continued)

(52) U.S. Cl.
CPC ............ *A61B 5/0088* (2013.01); *A61B 5/0086* (2013.01); *A61C 13/0004* (2013.01); *A61C 19/04* (2013.01)

(58) Field of Classification Search
CPC .. A61B 5/0088; A61B 5/0086; A61C 13/004; A61C 19/04
USPC .............. 433/29; 600/407, 473, 476; 382/128
See application file for complete search history.

(56) References Cited

U.S. PATENT DOCUMENTS

| 4,185,918 A | 1/1980 | DiMatteo et al. |
| 4,290,433 A | 9/1981 | Alfano |

(Continued)

FOREIGN PATENT DOCUMENTS

| WO | WO 94/20011 | 9/1994 |
| WO | WO 98/52460 | 11/1998 |

(Continued)

OTHER PUBLICATIONS

Written Opinion of the International Searching Authority, PCT/US2006/047056, Korean Intellectual Property Office, Apr. 30, 2007.

(Continued)

*Primary Examiner* — Heidi M Eide
(74) *Attorney, Agent, or Firm* — Klarquist Sparkman, LLP

(57) ABSTRACT

Dental imaging systems include an optical scanner that scans one or more interrogation beams across a portion of at least one tooth to produce a dentally modulated light flux associated with light scattering, absorption, or other interaction of the interrogation beam and a tooth interior. The dentally modulated light flux is detected and processed to produce picture information associated with the tooth. Interrogation wavelengths between 800 nm and 1800 nm can be used to provide images suitable for diagnosis and assessment of demineralization or other defects. Interrogation beams at one or more wavelengths can be used. Multiple detectors can be situated to receive dentally modulated light fluxes at different wavelengths or dentally modulated light fluxes with different directions or different locations. Markers at or on a tooth can be used to for depth determination. Index matching to the tooth can improve image quality.

22 Claims, 13 Drawing Sheets

(51) Int. Cl.
  *A61C 13/00* (2006.01)
  *A61C 19/04* (2006.01)

(56) References Cited

U.S. PATENT DOCUMENTS

| | | |
|---|---|---|
| 4,468,197 A | 8/1984 | Provost |
| 4,479,499 A | 10/1984 | Alfano |
| 4,935,635 A | 6/1990 | O'Harra |
| 5,570,182 A | 10/1996 | Nathel et al. |
| 5,818,587 A | 10/1998 | Devaraj et al. |
| 6,052,100 A | 4/2000 | Soltan et al. |
| 6,135,774 A | 10/2000 | Hack et al. |
| 6,201,880 B1 | 3/2001 | Elbaum et al. |
| 6,243,601 B1 | 6/2001 | Wist |
| 6,294,775 B1 | 9/2001 | Furness |
| 6,584,341 B1 | 6/2003 | Madelis et al. |
| 6,947,038 B1 | 9/2005 | Anh et al. |
| 7,142,312 B2 | 11/2006 | Quadling et al. |
| 7,536,234 B2 | 5/2009 | Kopelman et al. |
| 2004/0201856 A1 | 10/2004 | Quadling et al. |
| 2004/0254476 A1 | 12/2004 | Quadling et al. |
| 2005/0024646 A1 | 2/2005 | Quadling et al. |

FOREIGN PATENT DOCUMENTS

| | | |
|---|---|---|
| WO | WO 00/16691 | 3/2000 |
| WO | WO 2005/013843 | 2/2005 |

OTHER PUBLICATIONS

International Search Report, PCT/US2006/047056, Korean Intellectual Property Office, Apr. 30, 2007.

M. Kempe, A. Z. Genack, W. Rudolph, and P. Dorn, "Ballistic and diffuse light detection in confocal and heterodyne imaging systems," J. Opt. Soc. Am. A 14, 216-223 (Jan. 1997).

Brian W. Pogue and Tayyaba Hasan, "Quantitative fluorescence measurements from tissue using confocal detection," Proc. SPIE 2975, Laser-Tissue Interaction VIII, 202-207 (Jun. 16, 1997).

Extended European Search Report from European Patent Application No. 06845120.2, dated Nov. 6, 2014 7 pages.

Examiner's Report from Canada Patent Application No. 2,632,557, dated Jun. 12, 2014, 4 pages.

INFRARED DENTAL IMAGING

CROSS-REFERENCE TO RELATED APPLICATIONS

This application is a continuation of U.S. patent application Ser. No. 11/636,177, filed Dec. 8, 2006, now U.S. Pat. No. 8,556,625, which claims the benefit of U.S. Provisional Application 60/748,809, filed Dec. 8, 2005, both of which are incorporated herein by reference in their entirety.

TECHNICAL FIELD

The disclosure pertains to methods and apparatus for using infrared light to create pictures of teeth for assessment and treatment.

BACKGROUND

X-ray imaging is useful in dentistry because it reveals information about the inside of a tooth. This includes cavities or voids in the dental tissue, and also includes demineralized areas where the mineral content of the tissue has been reduced and the tissue becomes porous, typically as a result of acid in contact with the tooth. X-ray imaging works because cavitated or demineralized areas are more transparent to x-rays than surrounding tissues, and therefore transmit a higher intensity of the x-rays emanating from a source, creating a greater exposure on photographic film or on an electronic imaging device than the exposure created by radiation coming along nearby paths that do not intercept cavitated or demineralized zones. Since x-rays travel in nearly straight lines through the tooth, imaging is generally accomplished, not by focusing with a lens, but by using a very small source for the x-rays, so that a graded shadow is produced on the film or electronic detector. The size of the source will determine the degree to which the image is sharp or blurry.

X-ray imaging has several disadvantages. X-rays ionize molecules in living tissue and are therefore dangerous. The contrast in x-ray images of small caries is poor, because a small carious volume with increased transparency or reduced attenuation only makes a small fractional change in the intensity of transmitted radiation even if the carious region is perfectly transparent, as when it is void of matter. Interproximal caries (on the sides of teeth) can often be seen despite this disadvantage because x-rays from these caries come through relatively little matter near the edges of the tooth. Occlusal caries (on or just below the biting surfaces of molars) often cannot be seen at all, because these biting surfaces are generally broad and flat, so that the x-rays are transmitted through a large amount of matter which is quite opaque, and because the fractional change due to caries is small. It would be valuable to observe the lateral extent of occlusal decay by looking vertically through the biting surfaces of molars, but X-rays can generally only be used through the sides of teeth (traversing horizontally when the patient's head is upright). Even if x-rays could be used vertically, the opacity due to the long distance through the dental tissue would probably make this geometry ineffective for viewing the lateral extent of occlusal decay.

In addition to the detection of caries, dentists need to detect cracks in teeth, particularly when replacing an old filling and deciding whether to apply another inlay (which is acceptable if there is no crack but problematic if there is one) or to apply a crown (which is indicated if there is a crack). But x-ray techniques are not reliable for detecting cracks. A crack may show if it happens to be aligned with the beam, but will not show at all if it is not aligned.

Attempts have been made to use visible light for detecting dental anomalies. These techniques avoid ionizing radiation. Unlike x-rays, however, visible light does not travel straight through a typical thickness of dental enamel or dentin, but is scattered randomly in all directions. This makes teeth appear milky white, and prevents detection of deep anomalies because the scattering seriously blurs the light. A commercial product that records digital images made with light in the visible wavelengths has been shown to be quite ineffective for detecting and characterizing interproximal lesions in comparison to x-ray. See, for example, Young and Featherstone, "Comparing digital imaging fiber-optic trans-illumination, F-speed radiographic film, and polarized light microscopy," in *Early Detection of Dental Caries. III: Proceedings of the 6th Annual Indiana Conference*, G. K. Stookey, ed. (2003). This product can only detect anomalies that are on or very near the surface of the tooth, and cannot determine their depth or whether they have penetrated through the enamel and into the dentin, which is important for decisions on therapy.

Imaging with infrared light can reduce the problems with x-rays and visible-light imaging because dental enamel is substantially more transparent to infrared light than to visible light. But methods that use infrared cameras present additional problems. This disclosure describes some of those problems and presents methods and apparatus that mitigate them in ways that are suitable for practical, widespread commercial use of infrared dental imaging.

SUMMARY

Representative dental imaging systems disclosed herein comprise an interrogation optical scanner configured to scan an optical interrogation beam across at least a portion of at least one tooth, wherein the optical interrogation beam is substantially transmissible into the at least one tooth so as to produce a dentally modulated optical flux. An optical detection system is situated to produce a detection signal associated with the dentally modulated optical flux received from the at least one tooth, and a signal processor is coupled to receive the detection signal and produce position-dependent picture information associated with the at least one tooth based on the detection signal. In some examples, the signal processor is coupled to receive one or more scanner signals associated with a position of the interrogation beam on the at least one tooth. In some examples, a light source is configured to generate the optical interrogation beam at a wavelength of, or in a range of wavelengths greater than about 800 nm. Generally wavelengths or wavelength ranges are selected so that an interior of a tooth can be interrogated. In other examples, the wavelength or range of wavelengths of the optical interrogation beam is between about 1000 nm and 1800 nm. Wavelengths or ranges of wavelengths between about 1250 nm and 1350 nm and between about 1500 nm and 1600 nm are convenient. According to further examples, the light source is a laser diode or a light emitting diode.

According to representative examples, a modulator is configured to apply a modulation to the optical interrogation beam, wherein the signal processor is configured to identify the position-dependent picture information based on the applied modulation. The applied modulation can be a periodic modulation having a period that is less than approximately one dwell time of the interrogation beam, wherein the dwell time is a ratio of an interrogation beam width in a scanned direction divided by a speed at which the beam is scanned. In other representative examples, the applied modulation is at a frequency greater than the frequencies associated with the picture information or at a frequency distant from frequencies associated with interfering illumination such as ambient illumination.

According to some embodiments, an optical filter is situated with respect to the detection system so as to preferentially direct or conduct optical radiation associated with an interaction of the optical interrogation beam and the at least one tooth to the detection system. In further examples, the optical detection system comprises a first optical detector and a second optical detector that are configured to produce a first optical detection signal and a second optical detection signal, respectively. In still further additional examples, the optical interrogation beam includes an optical flux in a first wavelength range and an optical flux in a second wavelength range, and the first optical detector and the second optical detector produce the first optical detection signal and the second optical detection signal based on the optical flux in the first wavelength range and the second wavelength range, respectively.

In still other disclosed embodiments, the interrogation optical scanner includes a scan controller and an optical waveguide that has an output end configured to be selectively displaced in response to the scan controller, and the optical interrogation beam is associated with optical radiation exiting the output end of the optical waveguide. In a convenient example, the optical waveguide is an optical fiber. The interrogation optical scanner can include at least one rotatable mirror configured to scan the optical interrogation beam along at least one scan direction.

According to some examples, a dental display scanning system can be provided that includes a display optical scanner that directs an optical display beam onto a display surface. A modulation of the optical display beam is selected so as to produce a visible image of the tooth associated with the dentally modulated optical flux. The visible image of the tooth produced by the optical display can be formed on a surface of the at least one tooth, or on an image screen situated in proximity to the at least one tooth, or at other locations. In a particularly convenient example, the display optical scanner and the interrogation optical scanner are based on a common optical beam scanner that receives both an interrogation optical flux for delivery to the tooth and a display flux for forming the visible image. In some examples, a visible image is displayed that is based on a currently detected dentally modulated optical flux while in other examples a stored image is used.

In additional examples, an optical coupling device or radiation collector is configured to couple the dentally modulated optical flux to the optical detection system. The optical coupling device can include an imaging optical system situated to image a surface of the at least one tooth at the optical detection system or can include a light guide situated to direct the dentally modulated optical flux to the optical detection system. An optical coupling device can be considered to be either part of the optical detection system, or a separate element.

Dental imaging devices comprise an optically transmissive coupling surface having a predetermined surface shape and an optically transmissive conformable material in optical communication with the coupling surface, wherein the conformable material is configured to be conformable to a surface of a tooth. In representative examples, the coupling surface is provided on the conformable material. In additional examples, the coupling surface is provided on an optical window, and the conformable material contacts the optical window. The conformable material may be a fluid, a gel or a flexible solid, or a combination of theses. For purposes of this disclosure, "fluid" can include a gel or other material that can flow under sufficient pressure but maintains its shape under the mere force of gravity. Typically the predetermined surface shape of the coupling surface is substantially planar, but other surface shapes can be used. According to representative examples, a magnitude of a difference in an index of refraction of the conformable material and a refractive index of the tooth is less than a difference in the refractive index of the tooth and 1. In some examples, an index matching material can be applied to a tooth to reduce image contributions associated with surface features or to improve image contrast.

Dental imaging methods comprise scanning an interrogation beam on at least a portion of a tooth so as to produce a dentally modulated optical flux associated with the interior of the tooth, and processing the dentally modulated optical flux to obtain an image of the tooth. In some examples, the interrogation beam consists essentially of optical radiation at wavelengths between about 1000 nm and 1800 nm. In additional examples, the interrogation beam is directed to the tooth through an index matching material such as a fluid or gel applied to the tooth. In alternative embodiments, the index matching material is a solid material that is conformed to the tooth surface. In some embodiments, an image of the tooth is formed in proximity to the tooth based on the dentally modulated flux. In other examples, the image of the tooth is formed on a surface of the tooth.

In additional representative methods, scanning the interrogation beam comprises scanning a first interrogation beam and a second interrogation beam at a first wavelength and a second wavelength, respectively. Corresponding dentally modulated optical fluxes are processed to form at least one image of the tooth. In some examples, the first interrogation beam and the second interrogation beam are scanned substantially simultaneously on the tooth. In a convenient example, an optical interrogation beam and a display beam are scanned with a common scanner. In additional examples, at least one marker is provided on or near a tooth surface so as to provide a depth indication in the image.

Dental imaging systems comprise an optical system configured to produce at least a first image and second image associated with an interior of a tooth viewed from respective positions or directions, and at least one marker situated at or near a surface of the tooth and positioned so as to provide an indication of depth based on the first image and the second image. In some examples, the at least one marker is provided on a surface of a tooth. In other examples, the at least one marker is provided on a light coupling device.

The above examples are representative of some features of the disclosed technology. These and other features and aspects of the disclosed methods and apparatus are set forth below with reference to the accompanying drawings.

DETAILED DESCRIPTION

Figure 1:
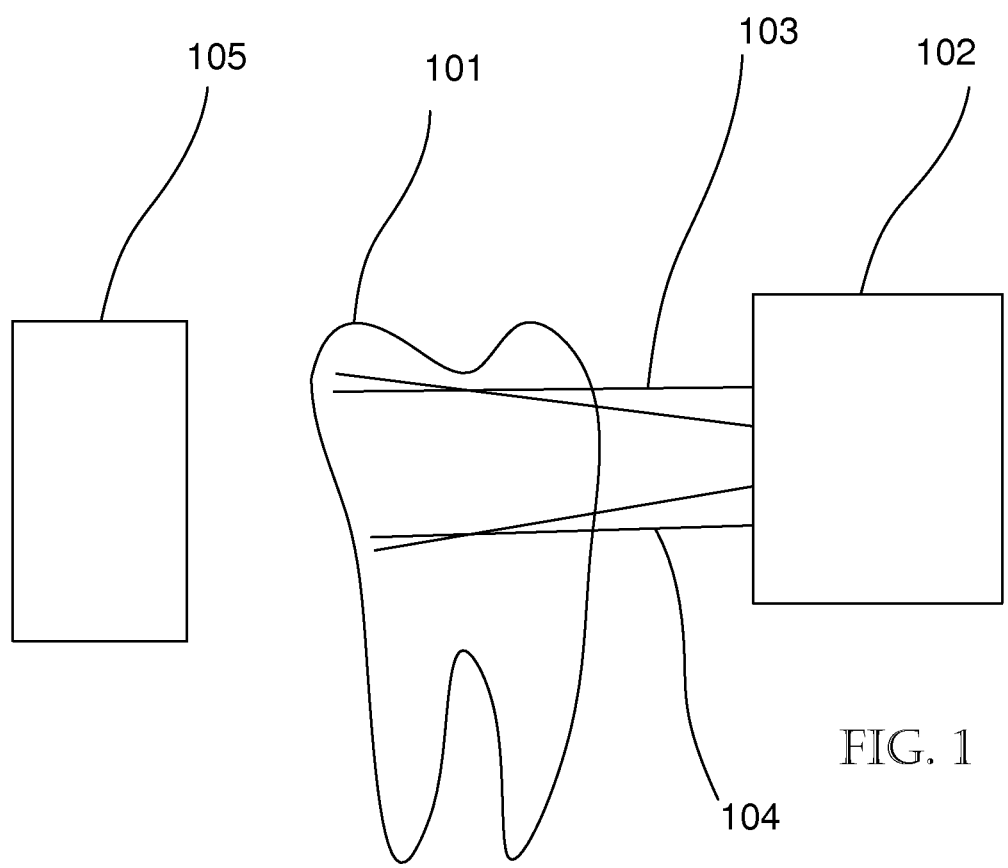
FIG. 1 is a schematic diagram showing a dental imaging system that includes an optical scanner that scans a focused interrogation optical beam through an interior of a tooth.

As used herein, the singular forms "a," "an," and "the" include the plural forms unless the context clearly dictates otherwise. Additionally, the term "includes" means "comprises." Further, the term "coupled" means electrically, electromagnetically, or optically connected or linked and does not exclude the presence of intermediate elements between the coupled items.

The described systems, apparatus, and methods should not be construed as limiting in any way. Instead, the present disclosure is directed toward all novel and nonobvious features and aspects of the various disclosed embodiments, alone and in various combinations and sub-combinations with one another. The disclosed systems, methods, and apparatus are not limited to any specific aspect or feature or combination thereof, nor do the disclosed systems, methods, and apparatus require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus.

Optical scanners generally receive an optical illumination flux and provide an interrogation beam that is scanned over a target surface. Generally, the interrogation beam is collimated, focused, or otherwise configured so that an illuminated "spot" can be scanned over the target surface or throughout a target volume. As noted below, in typical examples, a wavelength or wavelength range of the optical interrogation beam is selected to be substantially transmitted into a tooth so that the beam is scanned throughout at least portions of the tooth volume. Portions of the optical interrogation beam scattered, transmitted, or otherwise modulated by interaction with a tooth can be referred to as dentally modulated. In some examples, an optical scanner receives a collimated beam as an input and additional optical beam shaping is unnecessary, while in other examples, the optical scanner includes lenses, mirrors, or other beam shaping elements that process an input optical illumination flux so as to produce a collimated or focused beam, or otherwise provide an illuminated spot at the target. Spatially coherent light sources such as lasers, particularly diode lasers, are convenient, but other light sources such as light emitting diodes can be used. Optical scanners can be conveniently implemented using galvanometers, rotating polygonal mirrors, electro-optic or acousto-optic materials, or other types of scanners. In some examples described herein, scanning is based on spatial displacements of a vibrating optical fiber or on a microelectromechanical system (MEMS).

While in convenient examples, an interrogation beam is scanned with respect to a tooth, and dentally modulated radiation is detected with a fixed detector, in other examples, a fixed illumination is applied to the tooth, and an effective detection area is scanned with respect to the tooth. Typically, systems based on scanned interrogation beams instead of scanned detection provide superior signal to noise ratio.

In the disclosed examples, images or picture information associated with a tooth, a portion of a tooth, or portions or all of more than one tooth can be obtained. For convenience herein, the term "tooth" refers to a portion or portions of one or more teeth.

In some implementations, an optical scanner provides a scanned spot that traverses a two-dimensional raster. For example, the spot can be periodically scanned across the target horizontally but slightly vertically displaced between each horizontal scan. Such a raster scan can be convenient, but in other examples the optical scanner provides a scanned spot that traverses a series of circular arcs, a spiral, or a series of Lissajous figures or other patterns. Typically the optical scanner either receives or produces one or more scanning signals that are associated with a position of the scanned spot. Thus, based on such scanning signals, portions of the dentally modulated optical flux received at a detector (or a plurality of detectors) as a function of time can be processed to obtain received light flux as a function of location on, in, or at the target. A magnitude of received light flux as a function of position is referred to herein as an image or image signal or picture information, and can be provided either as a time-varying electrical signal or as a computer readable data file in formats such as a Tagged Image File Format (TIFF), a bitmap, or based on a standard such a JPEG or other standard or using other data file formats. It can also be provided as a visible picture.

In typical applications, control of ambient illumination can be inconvenient, difficult, or impractical. For example, placement of the optical systems needed for investigation of one or more teeth can be facilitated by illuminating a patient's mouth and providing ample room illumination. Such illumination or other illumination that is not associated with interrogation of one or more teeth can be reduced, eliminated or otherwise suppressed using optical filters such that only wavelengths associated with the interrogation beam are substantially received at the detection system. Such filters can be narrow-band thin film optical filters, colored (absorbing) optical filters, or polarizing filters. In some examples, the interrogation beam is polarized, and a polarizer is situated so that portions of the interrogation beam scattered by one or more teeth are preferentially delivered to the detector while the direct (unscattered) interrogation beam is attenuated. Typically, the interrogation beam is linearly or circularly polarized, and a polarizer is situated so as to substantially transmit an orthogonal linear or circular polarization to the detector.

In other examples, contributions of ambient illumination or other unwanted illumination, or electrical signals that do not correspond to properties of a tooth under investigation can be compensated or reduced by providing a modulation to the interrogation beam with, for example, an optical modulator such as a liquid crystal or electro-optic modulator, or modulating the electrical drive signal to an LED or laser diode. In some examples, such modulation is at a frequency large enough so that each scanned spot location is associated with at least one modulation period, i.e., at a frequency greater than a scanned beam velocity on a tooth divided by a width of the scanning beam.

Terms such as radiation, illumination, optical flux and the like are used herein to refer to electromagnetic radiation incident on and received from a tooth. Such electromagnetic radiation can be in a narrow frequency range (typical of lasers) or relatively broadband. In representative example systems described below, radiation at wavelengths between about 1250 nm and 1600 nm is used. However other wavelengths that suitably penetrate a tooth can be used. In some examples, a center wavelength is suitable to characterize a source spectrum, while for some source, center wavelength and one or more measures of spectral bandwidth are needed. These and other sources and wavelengths ranges are selected so the interrogation light flux can reveal internal features of teeth.

Certain details of dental diagnostic instrumentation and methods and resonant waveguides, including near-infrared transillumination imaging, are described in Waldmann et al., "Dental Diagnostic Instrument," PCT Published Patent Application WO 94/20011, Fried and Jones, "Near-Infrared Transillumination for the Imaging of Early Dental Decay," PCT Published Patent Application WO 2005/013843, and Seibel and Furness, "Miniature Image Acquisition System Using a Scanned Resonant Waveguide," U.S. Pat. No. 6,294,775, all of which are incorporated herein by reference.

Infrared light with a wavelength substantially longer than that of visible light, such as, for example, a wavelength of 1310 nanometers, has advantages over both x-rays and visible light. It can reveal interproximal lesions with high contrast, or show the shape and extent of occlusal lesions with a vertical view of molars, without exposure to the harmful ionizing radiation of x-rays. See, for example, Jones et al., "Near-infrared transillumination at 1310-nm for the imaging of early dental decay," OPTICS EXPRESS 11:2259 (September 2003), Graham et al., "Transillumination of Interproximal Caries Lesions with 830-nm Light," in *Lasers in Dentistry X*, Rechmann et al, eds., Proc. of SPIE, vol. 5313 (2004), and Bühler et al., "Imaging of occlusal dental caries (decay) with near-IR light at 1310-nm," OPTICS EXPRESS 13:573 (January 2005).

Infrared light can also show cracks in a tooth. Infrared light is effective because light scattering falls off rapidly as a function of increasing wavelength so that enamel becomes nearly transparent, almost like glass, at longer wavelengths. The dentin, in the center of the tooth, remains highly scattering even at longer wavelengths, but the transparency of healthy enamel is sufficient to make infrared light very useful. There is some absorption, which merely reduces the intensity but does not cause blurring the way scattering does. Demineralized regions of the enamel scatter and/or absorb light out of the beam, so that they transmit less light in a straight line than the unaltered enamel, rather than transmitting more as with x-ray. A small demineralized lesion can create a greater fractional change in transmitted infrared intensity than x-ray intensity, i.e., the contrast can be considerably higher. This has been tested by illuminating a tooth on one side with a 1310 nm light source, and using a lens to image the tooth from another side onto an infrared detector array that converts the infrared optical image to electronic signals that can be digitized and passed into a computer for display and/or storage of pictures. While 1310 nm is a convenient wavelength, infrared light having wavelengths between about 800 nm and 1800 nm can also be used.

While camera-based infrared techniques have excellent diagnostic value, the practice and commercial potential of these techniques are limited by the fact that the infrared detector array necessary for the long wavelength light is very expensive. Silicon-based CMOS and CCD array detectors that are used in video cameras and digital cameras are inexpensive, but the sensitivity of these devices declines rapidly as the wavelength increases beyond about 1000 nm or 1100 nm. For longer wavelengths such as 1310 nm or 1550 nm, InGaAs or another special material is necessary, and the manufacturing cost for fabricating the array is high. The present disclosure describes representative methods and apparatus based on different methods for obtaining an electronic picture that do not entail creating an optical image of the tooth in the infrared light, and do not require array detection. The disclosed methods and apparatus can be used with a much lower cost, and have other advantages as well.

In the examples described herein, position-resolved ("scanned") illumination and less-discriminate or diffuse detection is used instead of the position-resolved detection and less-discriminate or diffuse illumination used in camera-based systems. In a representative example, a single light detector is provided and a beam of light is rapidly scanned over a tooth in a pattern that covers an area, volume, or other region of interest. The detector receives light that comes through the tooth, either directly or by diffusion, scattering, or other process, and produces an electrical signal that is a function of time based on the received light. Because the position of the scanned beam on the tooth is also known as a function of time (typically based on scan voltages or other signals applied to or received from an optical scanner), we can combine these two sets of information to create a representation of the detector signal as a function of beam position. This information can be presented as a picture. In this sense, the photodetector signal can be transformed into "picture information," independently of whether or how it is actually displayed. The photodetector signal will be high for beam positions where light is coupled more efficiently from the source through the tooth to the photodetector, and low for beam positions where the signal is coupled more weakly; and we can assign different degrees of lightness or darkness to different signal levels in order to create a two-dimensional display, just as we would see if the photodetector were replaced with a light source, and the scanned-beam assembly were replaced with a long-wavelength electronic camera that uses a lens to create an optical image on an array detector.

A device that scans a spot of light over a surface is sometimes called a "flying-spot scanner." As described herein, the beam is scanned rather than a spot, because the beam passes into a volume of the tooth, instead of landing on a single surface that would create a spot. Different fractions of the optical power in the beam are scattered or otherwise interrupted by different portions of the tooth that it passes through, and reach the light detector by different paths that can be quite complex. But each location in the resulting picture is modulated by the optical properties of the tooth that are sampled by the corresponding beam location, and these optical properties are influenced by local anomalies in the tooth, so that the resulting picture gives a useful spatial indication of the anomalies. Such anomalies can be associated with light scattering, absorption, birefringence, or other optical properties. When the scanned-beam assembly projects light vertically into the biting surface of a molar, light penetrates the enamel and enters the dentin where it is scattered, making the dentin glow. A photodetector at the side of the tooth can detect this glow, even though no light from the scanned beam comes to the photodetector directly. The glow will be weaker when the beam intercepts a section of enamel that is demineralized, and this information can be used to display a darker area in the corresponding section of the picture that is generated.

For some positions and directions of the scanned beam, light will go through the tooth without encountering anything that scatters much of it. As an example, consider light going horizontally through a tooth, near the edge, so that it is inside the enamel only, not the dentin. When the beam is in an area where there is no interproximal demineralization there will be little scattering out of the beam. In this case, it is useful to place the detector on the far side of the tooth from the source; or, if it is placed elsewhere, to have some additional light coupling device for coupling at least part of the light emerging from the tooth into the detector. The detector signal will be high for such beam locations, but when the beam intercepts an area of demineralization the detector signal will be reduced because of light scattered out of the beam. As an alternative, however, we could place the detector at some other location so that it sees mainly light that is scattered out of the beam, and not directly transmitted light. For example, the detector could look down on the tooth from the top, or it could look at the dentin from some angle. For some alternatives, we expect the signal to be lower when the beam is not intercepting a demineralized zone, and higher when it is. There are many ways to deploy and to couple light into a detector, so that there will be contrast in the signal when the beam intercepts a region in the tooth that has altered scattering or absorption, to create a useful picture.

The substantial cost advantage of scanning methods has already been discussed, and cost has been noted as a serious disadvantage of conventional camera-based methods. In contrast to such conventional methods, the scanning methods disclosed herein demonstrate that high cost is not inherent in the general idea of deriving pictures from teeth using long-wavelength light. The disclosed methods provide practical, cost-effective alternatives to conventional methods. Additional advantages of the disclosed methods include: the elimination or reduction of saturation or clipping of bright regions of the image; the elimination or reduction of blooming, or of leakage of bright signals into nearby dimmer areas of a picture; the elimination or reduction of speckle when a laser is used as a light source; the potentially small size of the scanning device; the ability to use source modulation to reject stray light; ease of using multiple simultaneous detectors; and ease of changing the resolution. Representative systems that exhibit these and other advantages are described below.

Commercial detector arrays generally have limited dynamic range because the photocurrent for each individual detector or pixel must be integrated and stored on a capacitor while the signal is being read out from other pixels. (Without such integration, the signal-to-noise ratio would be poor.) Since the array circuitry limits the voltage or charge on the capacitor, this poses a limit on how bright a light can be measured. If it is too bright, the capacitor will simply charge up to its saturation value, and the true optical power level cannot be measured. But with the single detector used in some examples of this disclosure, there is no need to store charge, and the detector and its associated electronic circuit can accommodate an extremely large ratio of the brightest detectable signal to the weakest signal that is distinguishable from noise. This range can be enhanced by using nonlinear electronic circuitry such as a logarithmic amplifier, for which the output voltage is proportional to the logarithm of the detector photocurrent. Subsequent signal processing can reduce the information into a smaller dynamic range for display, or can apply a false-color mapping or a position-dependent mapping that depends on local signals, in order to make contrasting features in the tooth visible in all parts of the picture, in spite of the wide dynamic range of the signal.

Commercial detector arrays often exhibit "blooming" phenomena, in which applying a bright or over-saturating light level to one pixel will cause signal to leak into nearby pixels, so that the resulting picture shows a bright spot spreading beyond its actual boundaries, obscuring nearby dimmer parts of the picture. This can be avoided with the disclosed methods, because the electronic circuitry associated with the detector can easily be made so that it does not saturate, or so that it recovers very quickly even if it does saturate, so that the signal at one instant of time (corresponding to one location on the tooth) will be independent of or substantially independent of the signal at another instant (corresponding to another location), even if the corresponding locations are quite close. As a result of this, rapid measurements are possible over a much wider range of brightness values than is usually possible with array-detection devices. This reduces the need for devices such as crossed polarizers, such as have been used to eliminate direct light from the source in a system that uses a camera or array detector. Notwithstanding the advantage of eliminating polarizers for preventing blooming, the disclosed methods and apparatus can use polarizers for contrast enhancement.

It is convenient to use a diode laser for a light source, partly because such sources have been developed for telecommunications in the wavelength range of interest, and are readily available at low cost in a variety of wavelengths. But if a laser is used in the conventional method, there will be "speckle," or a complex granular multi-path interference pattern, at the surface of the array detector, which gives the optical image a coarse grain. To avoid this, a superluminescent diode has been used, which is related to a diode laser except that it emits incoherently over a broad range of wavelengths. Unfortunately, these devices are considerably more expensive than lasers, and are not readily available in as wide a range of center wavelength values. When the disclosed methods are used, speckle is absent or greatly suppressed even if the light source is a laser. A speckle pattern will, in fact, exist in the plane of the detector. But unlike the individual detectors in an array-detector device, this detector can be made large compared to the grain size of the speckle pattern. The speckle pattern will fluctuate as the beam is scanned, adding noise to the picture information; but fluctuations of different regions or grains will be poorly correlated so that, provided the detector is moderately large, the fractional fluctuation of the average intensity seen by the detector will be small.

Commercial detector arrays and their associated packages are somewhat large. In contrast, some scanning devices can be made very tiny, so that they do not compromise the ergonomics and other design aspects of a system for making pictures of teeth using infrared light. Not all systems and apparatus as disclosed herein are necessarily small, but several, including MEMS-based mirrors and a vibrating optical fiber, can be made extremely small.

Dental offices are usually brightly lit so that stray light can enter a light-detection system or device, whether a detector array or a single detector. This is a problem not only because it might saturate the detector, but also because stray light can be time varying. Variations will result, for example, from motion and shadows or from intensity modulation at twice the power-line frequency, and this can affect the picture. One way to reduce this problem is to place a filter in front of the detector that has a narrow spectral bandwidth centered at the infrared wavelength of the light source that is being used. Such a filter is especially well suited for systems in which laser diodes or other narrow spectral width infra-red light sources are used. This filter can be avoided, however, if we encode the light source by modulating light intensity, and decode or demodulate it electronically or digitally after detection. For example, we can modulate the light source to produce a sinusoidal or square wave modulation at some frequency, and then do lock-in detection, narrow band detection, or phase sensitive detection on the signal from the detector. Alternatively, we can measure the signal while the light source is on, and subtract a background signal obtained while the light source is off. Schemes like this can be most effective if the modulation frequency is quite high, far from any modulations that exist in the stray light. Typically, stray light modulation is primarily at frequencies less than about 1 kHz, and typically less than a low order harmonic of a power line frequency, i.e., less than about n60 Hz, wherein n is an integer less than about 10. High-frequency modulation and detection is difficult or impossible with an array of detectors, but easy to implement in scanning methods.

Two or more detectors can simultaneously receive light from the same scanned source, and this has several advantages. If a single source and detector are used (whether with a camera-based detection system or a position-resolved illumination (scanning) system, a magnitude or contrast of a dentally modulated optical signal received from one portion of a tooth may be satisfactory while from other portions the signal magnitude or contrast may be too low to obtain the desired dental image. With a camera or a detector-array-based system, this problem may be alleviated by using several light sources; but it is not possible to separate simultaneous information from the two sources. Using position-resolved illumination, dentally modulated optical signals from more than one detector can be either selected or combined in a way that varies with position and produces a preferred signal and/or contrast for any part of the field of view. Here "combined" means not just weighted addition, but also subtraction or other processing that exploits differences between the signals on two different detectors. Multiple detectors can be statically placed near a row of teeth, and then the scanned source can be moved and the data can be combined to produce an optimized image for each tooth or region of the row of teeth. Also, detectors can be differentiated on the basis of wavelength rather than merely position, and a combination of signals (including differences) can give improved contrast and resolution of dental lesions. Light of two different wavelengths or wavelength regions can be launched by the scanned source at the same time, and different detectors can select different wavelength bands by using optical filters.

Some scanning devices (including two-axis MEMS mirrors and resonant optical fibers) can switch their position resolution almost instantly, going between fast scanning with low position resolution and slower scanning with higher position resolution. This has a potential advantage in that the operator can quickly explore the teeth using low resolution, then hold the scanned source still while it records a slower but higher-resolution picture of a region of interest.

Representative Detection Methods and Apparatus

If a scanned beam impinges vertically on a tooth, it is possible to use a very small detector near the side of the tooth, because some light from the glowing dentin will reach it no matter where the beam is aimed. But when light is transmitted horizontally through a tooth, for some locations of the beam, light may go directly through the fairly transparent enamel without ever encountering dentin or other scattering material. In this case, it is useful either to have a large detector behind the tooth so that it will always intercept the beam, or to have a light-coupling device between the tooth and a smaller detector, so that the small detector will always receive some of the light coming through the tooth, no matter where the light exits the tooth. A smaller detector, which the light-coupling device enables, may be desirable for reduced cost. Also, the reduced electrical capacitance of a smaller detector may have advantages for the performance of an electronic amplifier associated with the detector. The light coupling device can incorporate scattering to divert light emerging from the tooth towards the detector, or it may incorporate a mirror surface or other reflection, such as total internal reflection as in an optical fiber, or a bundle of such fibers, or a rigid lightguide with internally reflective surfaces due either to a coating or a refractive index change near the surface. It can also incorporate imaging of the light emerging from the tooth, with a lens or other optical device, making either a sharp or blurry image of all or part of the tooth on the detector. In particular, a lens, curved reflector, or holographic optical element may be used to create a de-magnified image of a tooth on a detector that is considerably smaller than the tooth. Note that the optical image thus created is not related to the picture generated by the system, but is only for the purpose of coupling optical power from the tooth to the detector. However, this optical configuration can be arranged to provide a visible light picture in addition to coupling infra-red light to a detector.

If a small detector is used that can receive light from only a limited part of the tooth, the signal for different positions of the scanned beam may depend on where the detector is placed. Therefore, the use of a light-coupling device to couple the whole tooth somewhat uniformly to the detector can make the quality of the picture obtained less sensitive to the exact placement of the light-detection assembly. But alternatively the position sensitivity for a small detector can be exploited to enhance the information derived from the system, such as visibility or contrast or other clues about the presence and nature of anomalies. Such enhancement can be created by moving the detector to different locations, or by using several detectors simultaneously with different views of the tooth. As noted previously, multiple simultaneous detection of signals at different wavelengths or received at different locations is a particular advantage of the disclosed methods and apparatus. In this way, different pictures can be produced that are associated with the different wavelengths or different detector positions. Detected signals obtained during the same scanning operation will tend to ensure that every scanned region produces a useful signal level from at least one detector. The geometry of the picture information from different detectors will be the same because that is determined by where the beam is scanned. By obtaining images simultaneously based on different fixed detectors with a common scan pattern, rather than sequential images on a single detector that is moved, the resulting images can be overlaid or combined as needed, without the unpredictable offsets that can be associated with obtaining multiple images at different times. Simultaneous measurement at multiple detectors can also reduce measurement time.

Representative Scanning Methods and Apparatus

Scanning can be accomplished in a number of ways. If the object to be scanned were a flat surface, the light beam could have a large conical angle and could focus to a small spot on the surface. The smallness of this spot determines the sharpness of focus of the resulting picture; and moving the surface towards or away from the scanned-beam assembly would enlarge or blur the spot on the surface, degrading the spatial resolution. Because we want to detect details at different depths inside a three-dimensional tooth, it is better to make the light beam quite narrow, so that its cross section at any imaginary plane inside the tooth will be fairly small independently of whether the plane is nearer to or farther from the scanned-beam assembly. One way to make a scanned-beam assembly is to project a beam in a first direction towards a first mirror, which deflects it in a second direction towards a second mirror, which deflects it in a third direction. Rotating the two mirrors about appropriate axes, for example by galvanometer motors, will scan the beam direction in two directions. Another way is to deflect the beam with a single mirror that can be rotated about two different axes. This type of beam deflection can be implemented with MEMS technology and made both inexpensive and very compact. See, for example, Jain et al., "A Two-Axis Electrothermal Micromirror for Endoscopic Optical Coherence Tomography," IEEE J. Selected Topics in Quantum Elect. 10:636-642 (June 2004), which is incorporated herein by reference. Another scanning technique uses a beam emerging from an optical fiber, wherein the fiber is mounted with the fiber end projecting beyond the mount in cantilever fashion so that it can resonate. The mount is then vibrated so that the fiber end oscillates resonantly in a two-dimensional pattern. This scanning technique can be both inexpensive and very compact. See for example, Seibel and Furness, "Miniature Image Acquisition System Using a Scanned Resonant Waveguide," U.S. Pat. No. 6,294,775, which is incorporated herein by reference.

Another technique is to use a two-dimensional array of light sources that can be switched on and off, and a lens to project an image of this array towards the tooth. Scanning of the beam emitted by the assembly is accomplished by discretely turning on one light source at a time. Another technique uses a diffuse light source behind a two-dimensional array of light-gating devices, as is done in liquid crystal displays, and a lens to project an image of this array towards the tooth. Scanning is accomplished by discretely opening one light gate at a time. Another representative technique uses a one-dimensional array of sources or of light-gating devices (backed by a diffuse linear source), and a lens to project an image of this array towards the tooth, but to include in the path a rotatable mirror or other device that can scan the image in the direction perpendicular to the line of the array. For array devices, it is also possible to "scan" by using different patterns of multiple pixels, instead of turning on just one pixel at a time, and still generate picture information. For the purpose of this disclosure, scanning a beam includes not only moving a single beam, but also using a wider beam with narrow structured details that are varied.

In the different possible ways to construct the scanned-beam assembly, the internal structure can entail a beam that emanates approximately from a single point and changes direction, as with a two-axis MEMS-based mirror; a beam that emanates from a changing spatial location, as with an array of sources or optical gates; or a combination, as in the cantilevered optical fiber end, which changes both position and direction as it scans. In all of these, optics (such as a lens) and/or spatial separation can be incorporated in the scanned-beam assembly or used with it to convert the beam that is generated initially, in order to create the appropriate range of spatial scanning of the final beam at the tooth. Depending on the design, the direction of the beam at the tooth may or may not vary as the beam is scanned.

The beam may be focused to a small spot at the tooth. For finest resolution the beam might have a high numerical aperture, i.e. it might be a converging cone with a large angle to reduce the diffraction-limited size of the narrowest part of the beam; but this will compromise the depth of field, putting sections in different planes out of focus. For greater depth of field, the beam may have a smaller cone angle, or it may be essentially collimated; but collimation or a small cone angle will normally produce a beam that is wider, at its narrowest point, than the width that would result from a lager cone angle with a shorter depth of field. Alternatively, the distance of sharpest focus may be changed by moving the scanned-beam assembly or altering an internal part of it, in order to create different pictures that are focused sharply at different levels in the tooth.

When the beam enters the tooth at a point where the surface of the tooth is not perpendicular to the beam, refraction will cause it to bend. (In contrast, x-rays are not substantially bent when entering a tilted tooth surface.) This will distort the relationship between the position of a feature in space and the position where it appears in the resulting picture. That is not a problem for most diagnostic use, but it may be desirable to correct it for accurate geometric measurements. This can be done with a computational transformation of the digital picture if the tooth shape is known, but it may be advantageous to make an optical correction before the measurement. This can be done by placing an optical-correction device in contact with the tooth. As examples, this could be either a compliant transparent material (such as a flexible polymer), or a chamber containing a fluid or gel with an index of refraction that is roughly comparable to that of the enamel. In either case the surface that is away from the tooth, where the scanned beam first enters, would have a known shape (such as flat, or a sphere centered on a point from which all rays from the scanned-beam assembly emanate), so that either no correction is necessary, or a known correction can be applied to the image, to make its geometry accurate.

Representative System Implementations

The scanned-beam assembly and the detection assembly can be attached to each other as part of a single probe assembly, and positioned in the mouth by hand. Scanning can be fast, and visual pictures can be presented rapidly or in real time so that the operator can position the device to get the optimum image. Then the operator can signal the instrumentation to record a picture. A fast sequence of pictures can also be recorded as a movie. If the probe is moving during such a sequence, whether it is viewed in real time or later as a recorded movie, it will communicate useful three-dimensional information about the tooth as the perspective changes. Such three-dimensional information can also be extracted by comparing still pictures that view the tooth from different angles. For such analysis, it may be useful to place one or several marks or markers on or near the surface of the tooth, so that the relative position shifts of the marker(s) and features inside the tooth can be used to determine the depths of the features. If an optical correction device is used, such marks or markers can be provided on the optical correction device.

In other examples, the scanned-beam assembly and the detection assembly are on different probes that are not rigidly attached to permit the operator to change the positions of both independently in order to get the optimum contrast or other properties in the resulting picture. Alternatively, the scanned-beam assembly and the detection assembly can be included in a single assembly while a separate independent coupling device, such as a reflector or light scatterer or light conduit, is positioned near the tooth to alter the coupling of light from the tooth to the detection assembly, in order to get the best picture. In some examples, the scanned-beam assembly and the detection assembly couple to the tooth from substantially the same direction, and the two functions merge into a single assembly, that may share some optical component such as a lens. In additional examples, the scanned-beam assembly and/or the detection assembly are moved either automatically or manually around a region containing multiple teeth, creating a movie or series of pictures; and a computer is used to assemble this information into a composite picture of part or all of the patient's set of teeth.

Because absorption and other optical properties depend on the wavelength of the light, information can be obtained from the differences between pictures that are recorded with different wavelengths of light. Optically absorbing material can be put into porous or cavitated areas of a tooth to increase the optical contrast, and also to make the optical properties different at different wavelengths. Plain water has such wavelength-dependent properties, and is already present in higher concentrations in cavitated or demineralized zones than in healthy enamel. It has an absorption peak at a wavelength region near 1400 nanometers, and another peak in the vicinity of 2000 nanometers. See, for example, Jones and Fried, "Attenuation of 1310- and 1550-nm laser light through sound dental enamel," Proc. SPIE Vol. 4610, p. 187-190, in *Lasers in Dentistry VIII*, Rechmann et al., eds. (June 2002). These peaks permit us to select two close wavelengths for which the absorption values of a water-filled artifact differ much more than the absorption values for healthy enamel. We can combine two (or more) wavelengths in a single scanned-beam assembly, and switch between them either between alternating scans or very rapidly during a single scan of the field of view. Alternatively, we can launch two (or more) wavelengths simultaneously into the scanning assembly, and detect them simultaneously with different detectors. We can detect and distinguish them simultaneously with a single detector if the fluxes at the two wavelengths are modulated at different frequencies, or the same frequency with different phases, or in other different manners, by simultaneously demodulating the detector signal in two different ways. In a camera-based system, a tooth can be illuminated at two or more wavelengths using one or more light sources, and images at two or more wavelengths obtained sequentially with one camera or simultaneously with two cameras using fixed or sequentially switched optical filters, dichroic mirrors or other wavelength selective devices.

Besides conventional display methods, pictures can be displayed by using a beam-scanning assembly similar to the one that scans the infrared beam over the tooth, except that it uses a visible light source that is modulated. The light source intensity can be modulated synchronously with the scanning, so that a visible picture will be projected onto whatever surface the scanner is directed at. The surface can be reflective and scattering (like flat white paint) and viewed from the same side as the scanner; or it can be transmissive and scattering (like ground glass) and viewed from the opposite side. The display scanner can also be head-mounted with optics for projection into the eye with no screen besides the retina. If such a display scanner is driven simultaneously and synchronously with the infrared scanner, and the intensity of the visible light source is controlled by a signal derived from the signal from the infrared detector, a real-time display can be created. This can be inexpensive because it does not require fast digitizing, computing and digital storage. It can be constructed from purely analog electronic circuitry. In this case, the signal processor for converting the detector signal into picture information comprises the display system. We can combine the infrared scanner and the visible display scanner by multiplexing both the infrared light source and the modulated visible light source onto a single scanning device, so that the visible image is projected directly onto the tooth or a nearby screen, thus showing the operator exactly where dental artifacts are located. For this specific scanning display method, either spectral filtering or source encoding and decoding can be used to ensure that the detector responds only to the infrared light and not the visible light. For any such scanning display method, whether it projects onto a screen or the retina or the tooth, the contrast and visibility can be adjusted, either manually or automatically, by adjusting the parameters of a nonlinear function by which the detector signal controls the intensity of the display source. This adjustable nonlinear relationship can be implemented inexpensively in analog circuitry. It can also be implemented by digitizing the detector signal and combining this with either operator input or digital image analysis to determine what control signals to send to the visible light source. If it is done digitally, there may be advantage in delaying the display by one or an integer number of frames in order to allow time for the computation, instead of doing it in precise real time. This can permit the processing for each location to be based on the whole picture or a large region, instead of the instantaneous signal. Two or more modulated sources with different colors can also be combined onto the display scanner for a color display, permitting the use of false colors for enhancing contrast.

Representative arrangements are illustrated in the accompanying figures. In FIG. 1, a tooth 101 is adjacent to a scanned-beam assembly 102. A scanned light beam emerging from the scanned-beam assembly 102 is shown at two locations 103 and 104. The light beam converges to a focus inside the tooth 101. At any particular location, part of the light in the beam may go through the tooth to a detection assembly 105; part of it may be scattered away or absorbed by material in the tooth so that it never reaches the detector assembly; and part of it may be scattered or multiply scattered in a way that it eventually reaches the detector assembly 105 by a path that is not direct.

Figure 2:
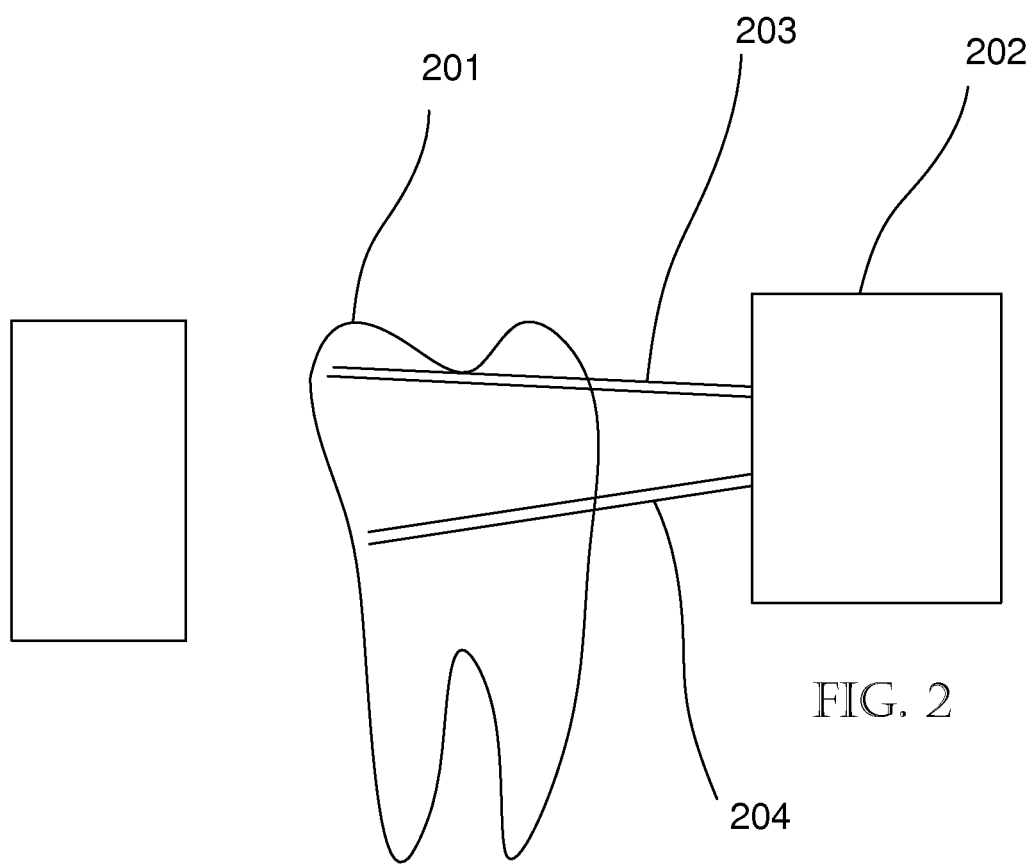
FIG. 2 is a schematic diagram showing a dental imaging system that includes an optical scanner that scans a narrow collimated optical beam through an interior of a tooth.

FIG. 2 illustrates a scanning system 202 that directs a nearly collimated scanned beam (shown as scanned to two representative locations 203, 204) to a tooth 201. As shown in FIG. 2, such a scanned beam has a relatively constant beam diameter or other beam cross-sectional area, but does not have as sharp a focus as the beam of FIG. 1. Nevertheless, a suitably small beam cross-sectional area can be produced that can be approximately the same throughout the tooth 201. In contrast, the conical beam of FIG. 1 has a larger cross-section at some points in the tooth.

Figure 3:
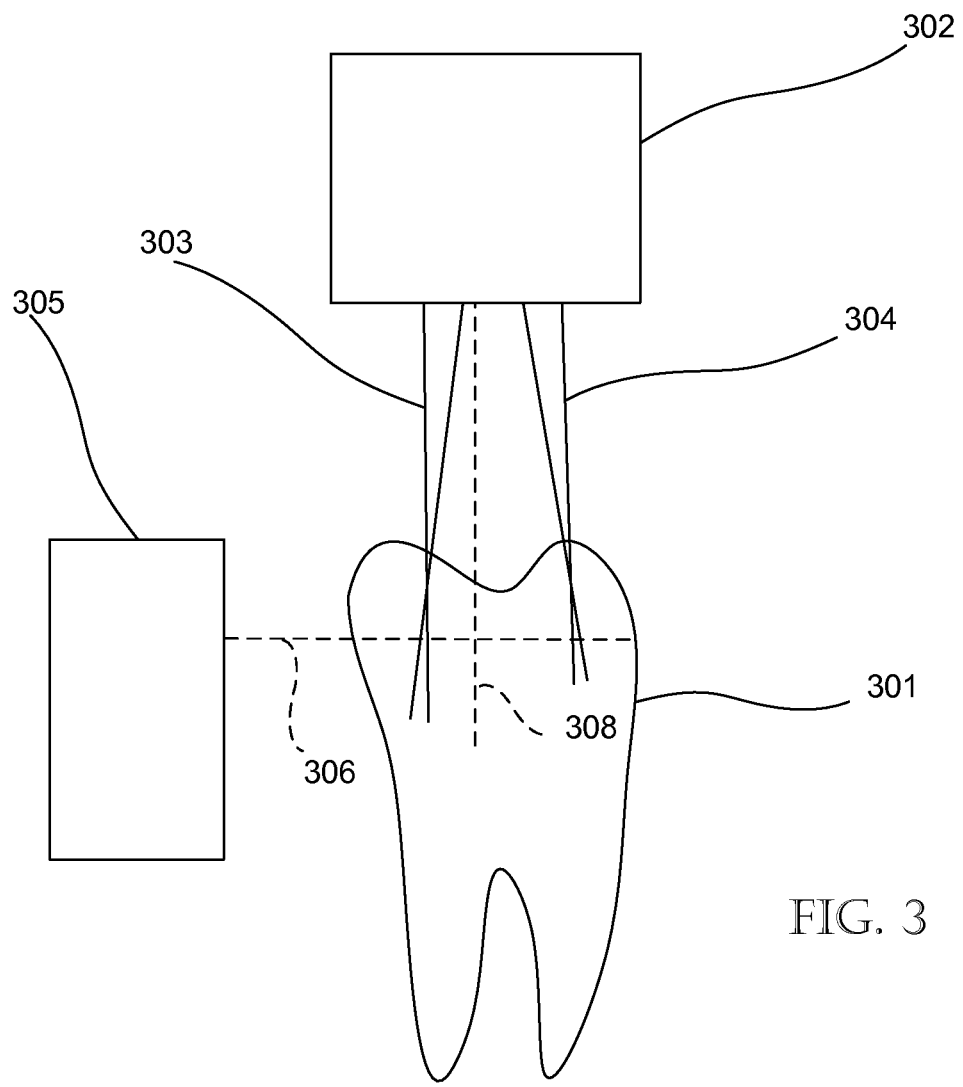
FIG. 3 is a schematic diagram that shows a dental imaging system in which a scanned interrogation beam is directed along an interrogation axis to a biting surface of tooth and a detector is situated at a side of the tooth along a detection axis that is not parallel to the interrogation axis.

FIG. 3 illustrates a scanning system 302 that directs a scanned beam (shown at locations 303, 304) to be vertically incident onto a biting surface of a tooth 301. A detection assembly 305 is situated along an axis 306 that is approximately perpendicular to an axis 308 along which the scanned beam is incident to the tooth 301. Other detector locations are possible, and a detector can be situated so as to have an axis that can be at any angle with respect to a direction of incidence of the scanned beam.

Figure 4:
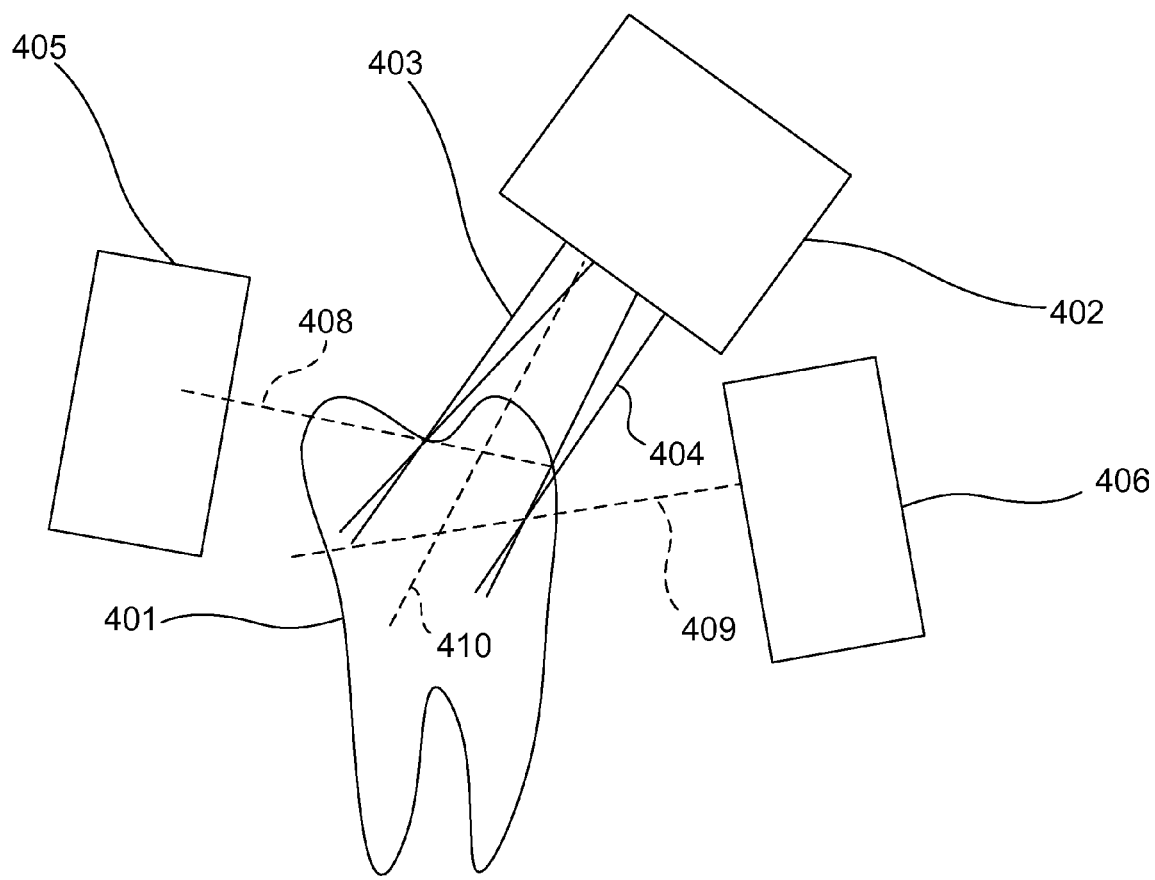
FIG. 4 is a schematic diagram that shows a dental imaging system in which a scanned interrogation beam is directed to a tooth and first and second detectors are situated at two different arbitrary detection locations.

FIG. 4 illustrates a dental imaging system that includes a scanning system 402 that directs a scanned beam (shown at representative locations 403, 404) to a tooth 401. Detection assemblies 405, 406 are situated along respective axes 408, 409 that are oriented at arbitrary angles with respect to an approximate axis of incidence 410 of the scanned beam at the tooth 401. As shown in FIG. 4, two or more detectors or detection assemblies can be used simultaneously. Even if a single detection assembly is used, a wide variety of orientations can be selected for both the detection assembly and the scanned-beam assembly. The detection assembly 406 is shown close to the scanned-beam assembly 402 and, in an extreme case that is not illustrated, a detection assembly can be situated at the scanned-beam assembly or be provided as part of a common assembly, so that a detected optical flux can be received that is approximately backscattered with respect to the a direction of propagation of the scanned beam.

Figure 5:
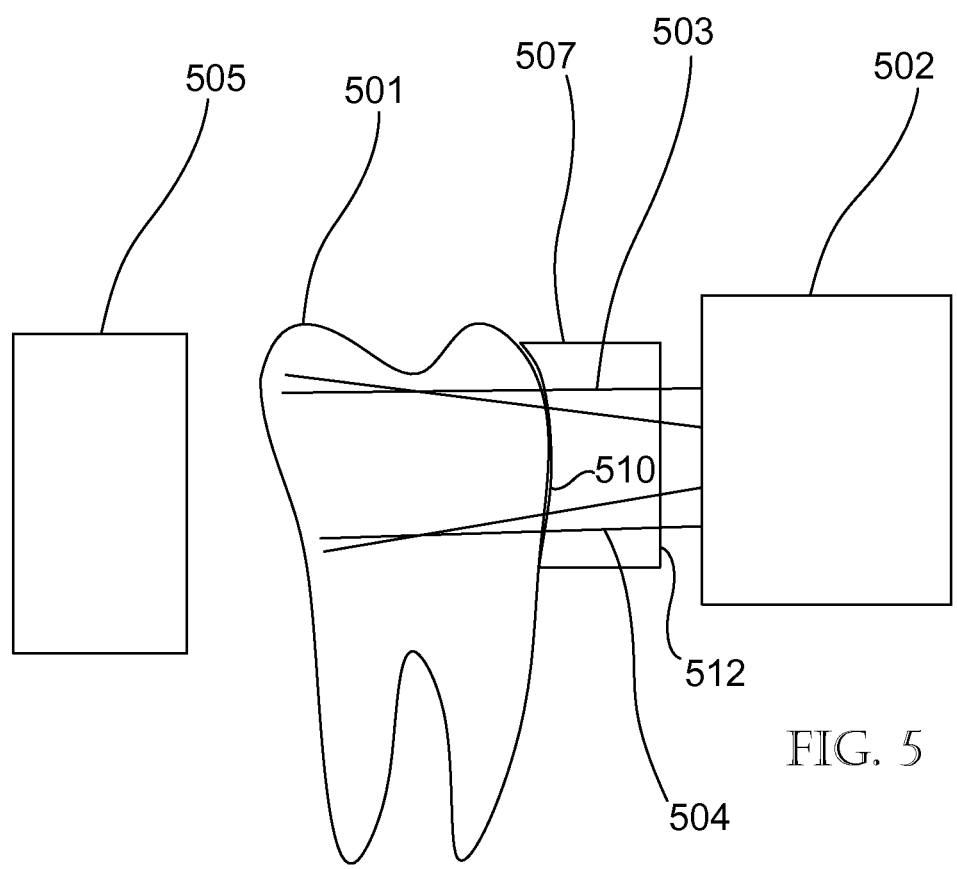
FIG. 5 illustrates a dental imaging system that includes an input coupling device comprising an optically transmissive compliant or fluid material that conforms to tooth shape and presents a known surface to a scanned-beam assembly for geometric correction.
Figure 6:
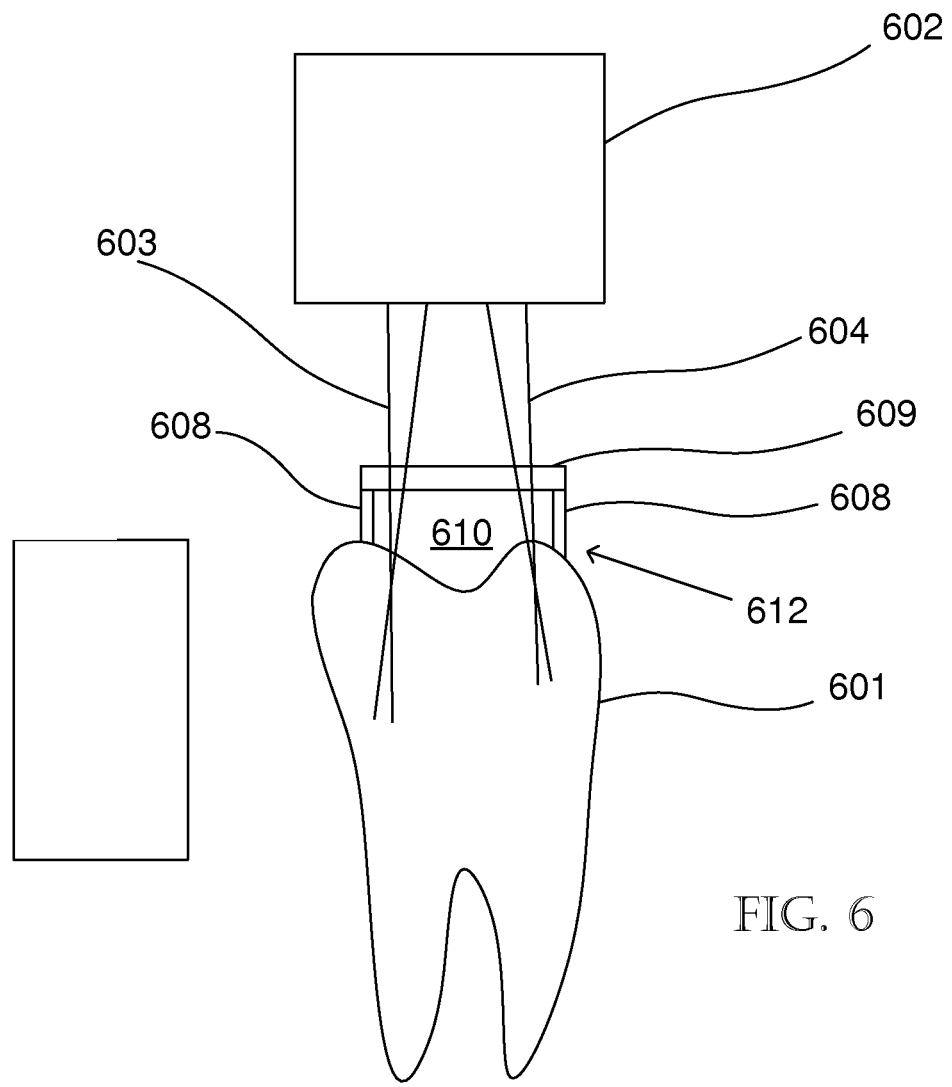
FIG. 6 illustrates a dental imaging system that includes an input coupling device comprising an optically transmissive compliant or fluid material that conforms to tooth shape. The input coupling device comprises a chamber with compliant edges containing an index-matching fluid or gel that conforms to the tooth shape.

FIG. 5 illustrates a scanning system that includes a scanned-beam assembly 502 that directs a scanned beam (shown at representative locations 503, 504) to a tooth 501. A dentally modulated light flux is received by a detection assembly 505. As shown in FIG. 5, an optical-correction device 507 is placed between the tooth 501 and the scanned-beam assembly 502. The optical-correction devices includes an exit surface 510 that is generally conformable to the surface of the tooth 501 and an entrance surface 512 having a predetermined shape. A flat entrance surface can be convenient, but the entrance surface 512 can have a spherical, elliptical, cylindrical, or other shape. In some examples, the entrance surface 512 is selected to focus or collimate an input scanned beam. Although FIG. 5 illustrates an optical-correction device in which one or more input beams are communicated to the tooth 501 along a straight line axis, in other examples, the optical-correction device can receive the beams at an entrance surface and then reflect the beam at an internal reflective surface toward the exit surface 510. The optical-correction device 507 is preferably formed of a material that is substantially transparent to the scanned beam and has an index of refraction that is closer to that of the tooth than air. An exact index match is unnecessary. An index of refraction is generally selected to reduce reflection and/or refraction at a surface of a tooth. The conformable exit surface 510 can be provided by a flexible polymer or gel, while the remaining portions of the optical-correction can be formed of a rigid transparent material such as glass or a clear plastic. Referring to FIG. 6, a scanned-beam assembly 602 is oriented vertically and is situated to direct a scanned beam (shown at representative locations 603, 604) to a tooth 601 through an optical correction device 612 that includes compliant walls 608 that contact the tooth 601 and a rigid transparent window 609, that in conjunction with the surface of the tooth 601 and the walls 608, define a chamber 610 that can be filled with, for example, water, a gel, an oil, glycerol or a sugar syrup. Although the chamber is shown as relatively tall for clarity, the walls 608 can be substantially shorter so that the volume of the chamber 610 can be reduced. An index matching material (such as index matching liquid or gel) can be injected through tubing attached to the chamber, and drawn off after recording a picture through similar tubing, but such tubing is not shown in FIG. 6. Alternatively, a gel filled chamber can be provided and pressed against the tooth, with excess gel forced out of the chamber in a direction selected so that excess gel does not interfere with imaging the tooth. The walls 608 of the chamber 610 do not necessarily need to seal tightly (and in some cases, such walls are unnecessary) because flow and/or viscosity or other phenomena can be used to maintain the fluid between the window 609 and the tooth 601. Thus, in some examples, an optical window can rest on a gel or fluid layer that contacts a tooth.

Figure 7:
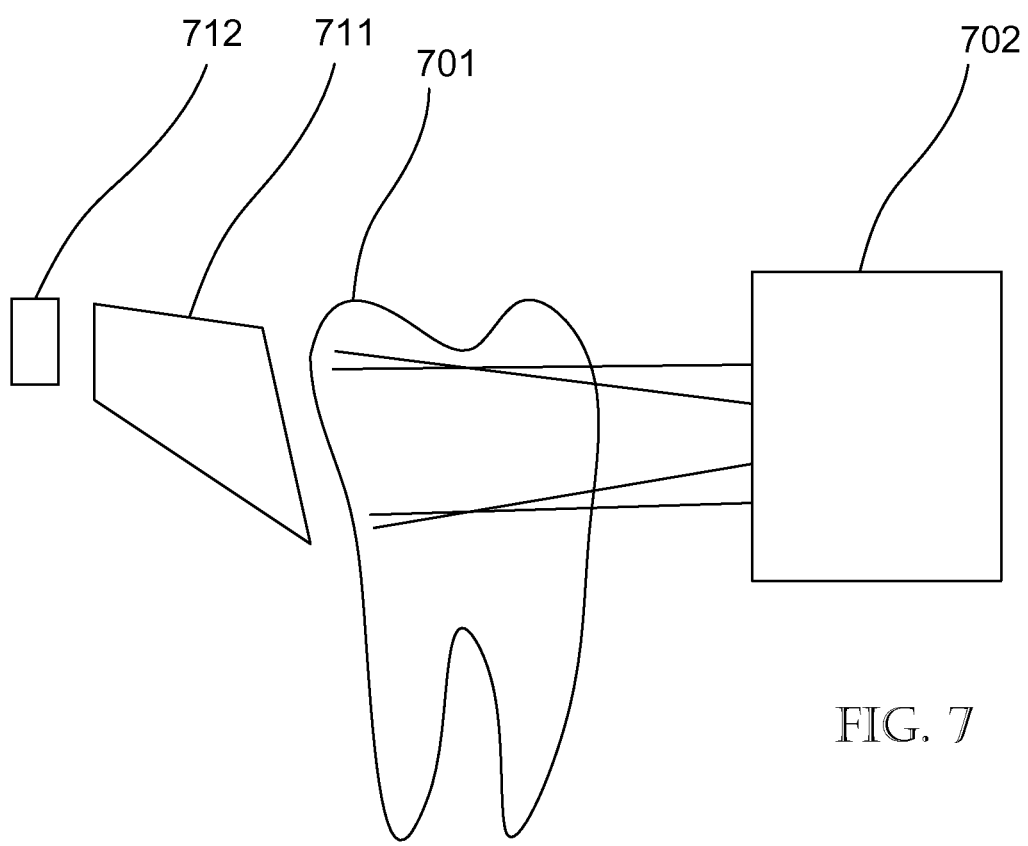
FIG. 7 illustrates a dental imaging system that includes a detector-coupling device situated to influence the coupling of dentally modulated optical flux to the detector.

FIG. 7 illustrates a detection assembly that comprises a relatively small detector 712 and a light-coupling device 711 that are situated so that the scanned-beam is directed or conducted from the tooth 701 to the detector 702. The combination of the detector 712 and the light-coupling device 711 can be referred to as a "detection assembly." Alternatively, the detector 712 can be referred to as a "detection assembly" and the light-coupling device 711 can be provided in a separate assembly.

The light-coupling device 711 can be configured so that portions of the dentally modulated optical flux from one or more selected areas of the tooth 701 are coupled to the detector 702. For example, an oblong or rectangular input surface of a light guide can be situated at or near a targeted tooth area so that flux from the targeted area is directed to the detector 702. The light guide can be tapered to have a circular or other cross-sectional area at an exit surface for convenient coupling to a round or square photosensitive area. Other shapes can also be used. Portions of the dentally modulated optical flux can also be selected by imaging a detector area onto the tooth 701 with a cylindrical lens to select an oblong area of the tooth 701. Alternatively, a spherical lens can be used to image the tooth surface, and portions of the image blocked with a plate that includes an aperture corresponding to a selected area of the tooth 701.

Figure 8:
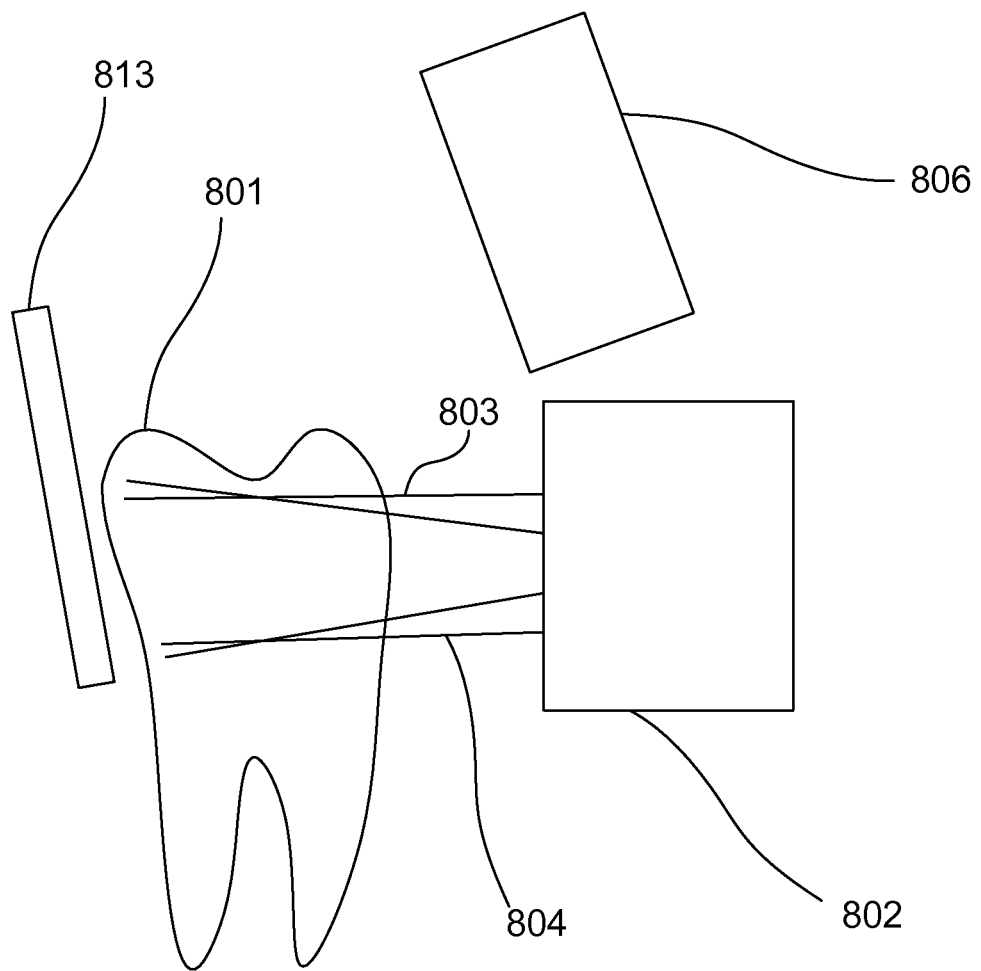
FIG. 8 illustrates a dental imaging system that includes a detector situated near the scanned-beam assembly and a detector-coupling device that comprises a reflector or scatterer on the far side of the tooth so as to direct dentally modulated light flux to the detector.

FIG. 8 illustrates a dental imaging system that includes a scanned-beam system 802 that directs a scanned beam (shown at representative locations 803, 804) to a tooth 801. A light-coupling device 813 is situated to direct an incident light flux to a detection assembly 806 that is situated on approximately the same side of the tooth 801 as the scanned-beam assembly 802. The detection assembly 806 is positioned so that it can receive light that is scattered or reflected directly from the tooth 801, and light that passes through or is scattered by the tooth 801 and directed to the detection assembly 806 by the light-coupling device 813. The light-coupling device can be, for example, a reflector such as a mirror, dichroic reflector, holographic reflector, or other device. The light-coupling device can be configured to selectively direct light associated with the scanned beam to the detection assembly 806 so as to reduce ambient light contributions to detected signals.

Figure 9:
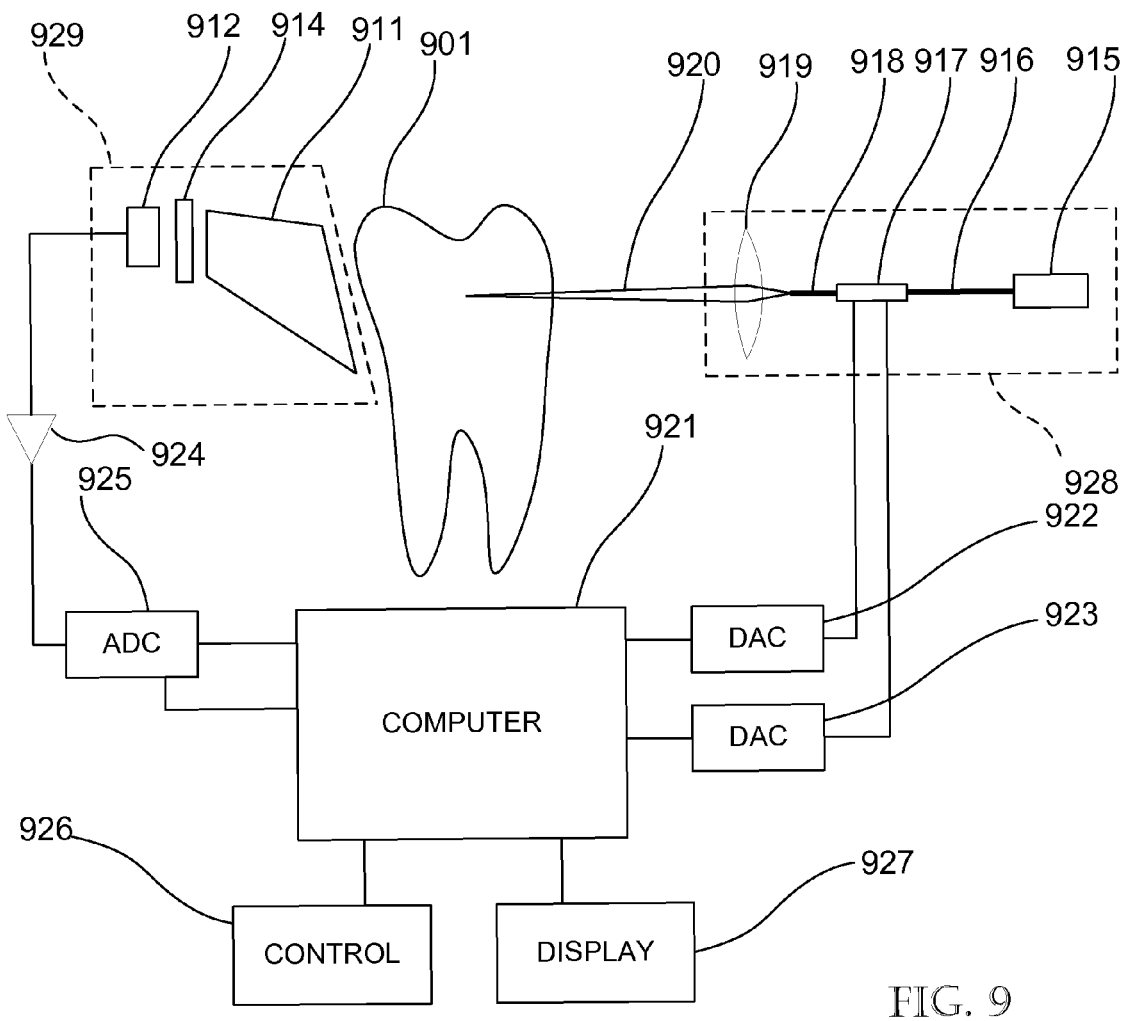
FIG. 9 is a schematic diagram of a system for obtaining infra-red pictures of teeth that includes a fiber-optic scanner.

FIG. 9 is a more complete illustration of a representative dental imaging system that includes a detector 912 coupled to receive a dentally modulated light flux from a tooth 901 with a light-coupling device 911. An optical band-pass filter 914 is situated in front of the detector 912 to eliminate or reduce most stray light by selecting only a narrow wavelength region centered at the wavelength of a laser 915 used to produce a scanned beam. The detector 912, filter 914, and light-coupling device 911 comprise a light-detection assembly 929, although the light-detection assembly 929 can include other components such as an amplifier 924 that converts a detector photocurrent into a voltage. The amplifier 924 or other signal processing apparatus can be provided separately or in combination with the light-detection assembly. In a convenient arrangement, the assembly 928 comprises a scanned-beam assembly that includes the laser 915 (such as a laser diode) that is coupled to a proximal end of an optical fiber 916 or other optical waveguide. A distal end 918 of the optical fiber 916 is secured to and protrudes in cantilever fashion from a two-axis piezoelectric actuator 917 that is driven in such a manner that the fiber end 918 oscillates in a pre-determined two-dimensional pattern. The fiber end 918 is imaged by a lens 919 onto a region of the tooth 901 or projected in a narrow beam 920 towards the tooth 901. A small motion of the fiber can be magnified by the lens 919 so that the pattern that is scanned by the beam at the tooth 901 is suitably large to cover a region of interest on or in the tooth. The two axes of the piezoelectric device 917 are driven by rapid sequences of voltages from digital-to-analog converters (DACS) 922, 923, respectively. The DACs 922, 923 can produce, for example, two sine-waves at a resonant frequency of the cantilevered fiber end 918 that are 90 degrees out of phase, but with amplitudes that start small and grow increasingly larger. These waveforms can be used to make the fiber end 919 oscillate in a circle with growing amplitude, i.e., the fiber end moves in a spiral that can be selected to densely cover a circular area. A corresponding area on the tooth 901 is scanned. If the resonant frequency is moderately high, such as 5 kHz, a reasonably dense area can be scanned in about 0.1 second or less.

A computer 921 or other control device can be arranged to provide appropriate digital drive values to the DACs to produce a selected scan pattern, scan area, scan rate, or other scanning parameter. A desktop, laptop, palmtop, or other processing system can be used, and scanning parameters can be selected based on user inputs provided with, for example, a graphical user interface via a pointing device, keyboard, or other input device. The computer 921 also receives digitized data from the analog-to-digital converter 925 based on the detection signal coupled from the detector amplifier 924. Two lines are shown between the analog-to-digital converter 925 and the computer 921 because the computer 921 not only receives digital data, but it controls the times when the analog-to-digital conversions occur, synchronously with the signals that it sends to the digital-to-analog converters 922, 923. In this manner, the position of the scanned beam 920 is known for each measurement of the detector signal, so that the data can be used to construct a picture.

The computer 921 is also shown attached to a user input device 926 configured to receive control information from the operator, such as commands to start scanning, to record a picture, and to store information on which tooth in the patient's mouth the picture portrays. Suitable user input devices include keyboards, pushbuttons, pointing devices such as mice, foot pedals, microphones coupled to voice-recognition software, and/or other devices. The computer 921 can also be coupled to store any dental images directly in patient database or in a patient electronic file, or to transmit the images over a local area network, or a wide area network such as the Internet for remote storage or evaluation. Typically the computer 921 includes or is coupled to a display 927 that is configured to display dental pictures as well as image acquisition and control parameters, patient dental records, and other data. The system of FIG. 9 is only a representative example, and other configurations can be used.

Figure 10:
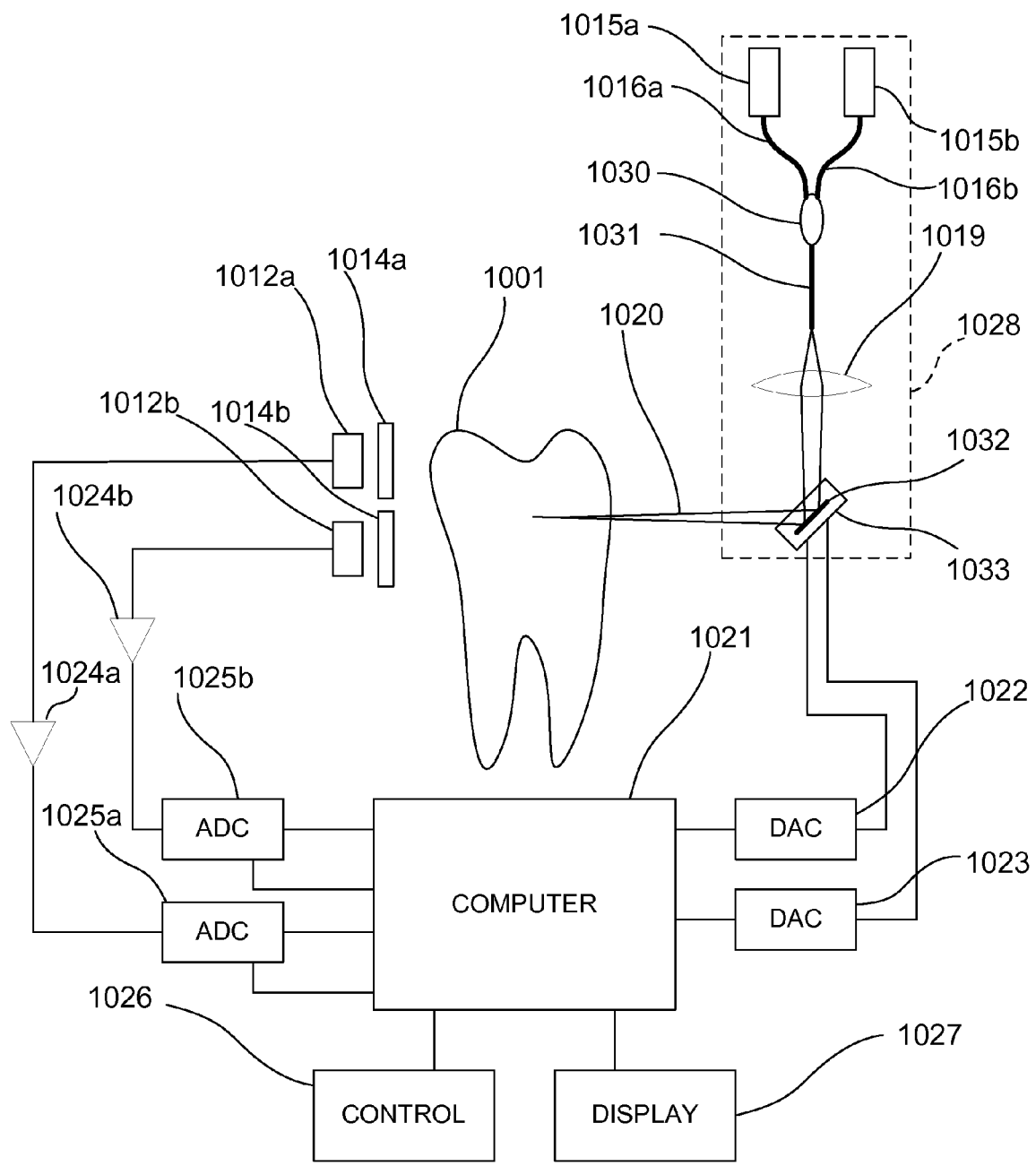
FIG. 10 is a schematic diagram of a system for obtaining infra-red pictures of teeth that includes a micro-electromechanical system (MEMS) scanner.

Referring to FIG. 10, a dental imaging system includes a scanned-beam assembly 1028 that include laser diodes 1015a, 1015b that are coupled to respective optical fibers 1016a, 1016b. A fiber coupler 1030 combines the optical fluxes of the laser diodes 1015a, 1015b in an output fiber 1031. In some examples, these fibers are single-mode fibers. The combined fluxes exit the output fiber 1031 and a lens 1019 processes the combined fluxes to produce an interrogation beam 1020 that is scanned over at least a portion of a tooth 1001 by a micro-electromechanical (MEMS) scanner 1033 that includes a rotatable mirror 1032. The MEMS scanner 1033 is coupled to DACs 1022, 1023 that produce scanning signals under the control of a computer 1021 for activation of the rotatable mirror 1032. For dual wavelength operation, emission wavelengths of the laser diodes 1015a, 1015b are different. In some examples, one of the laser diodes 1015a, 1015b can be selected to produce a visible image on the tooth by modulating its intensity. A MEMS scanner can be convenient, but other optical scanners can be used.

The rotatable mirror 1032 can be rotatable about two axes in response to sequences of voltages from the DACS 1022, 1023. As an example, the waveforms can be two square waves at frequencies close to twice the resonant frequencies for the two axes of the MEMS scanner 1033, each square wave oscillating between zero volts and some non-zero value. For some MEMS devices, such a waveform will impart kinetic energy to the oscillating mirror by attracting it electrostatically towards its center position each time it approaches the center position. By adjustment of the frequencies of the two square waves, the reflected beam 1020 can be made to scan a repeating Lissajous pattern, with a repetition rate and a density of scan lines that is determined by the exact ratio of the two frequencies. In other examples, the MEMS scanner 1033 can be electrothermally activated.

Photodetectors 1012a, 1012b are coupled to amplifiers 1024a, 1024b, respectively. Bandpass optical filters 1014a, 1014b can be provided for the detectors 1012a, 1012b so that image signals or picture data associated with the two different wavelengths can be obtained simultaneously (i.e., in the same scan), and ambient light fluxes can be attenuated. The outputs of the amplifiers 1024a, 1024b are coupled to respective analog-to-digital (ADC) converters 1025a, 1025b that provide digitized detection signals to the computer 1021 that processes the digitized detection signals to provide picture information based on the scanning signals. A display 1027 is provided to display dental images or patient data as well as to provide a control interface for image acquisition in combination with a control device or control devices 1026. The display 1027 can be configured to display a composite dental image based on information from the two wavelengths. Two separate pictures can be displayed side by side, or a single picture might be generated by the computer 1021 by, for example, using differences between the two pictures to enhance the contrast of anomalous features in the tooth. Although FIG. 10 is a practical embodiment, it is only an example, as many other configurations are possible.

Figure 11:
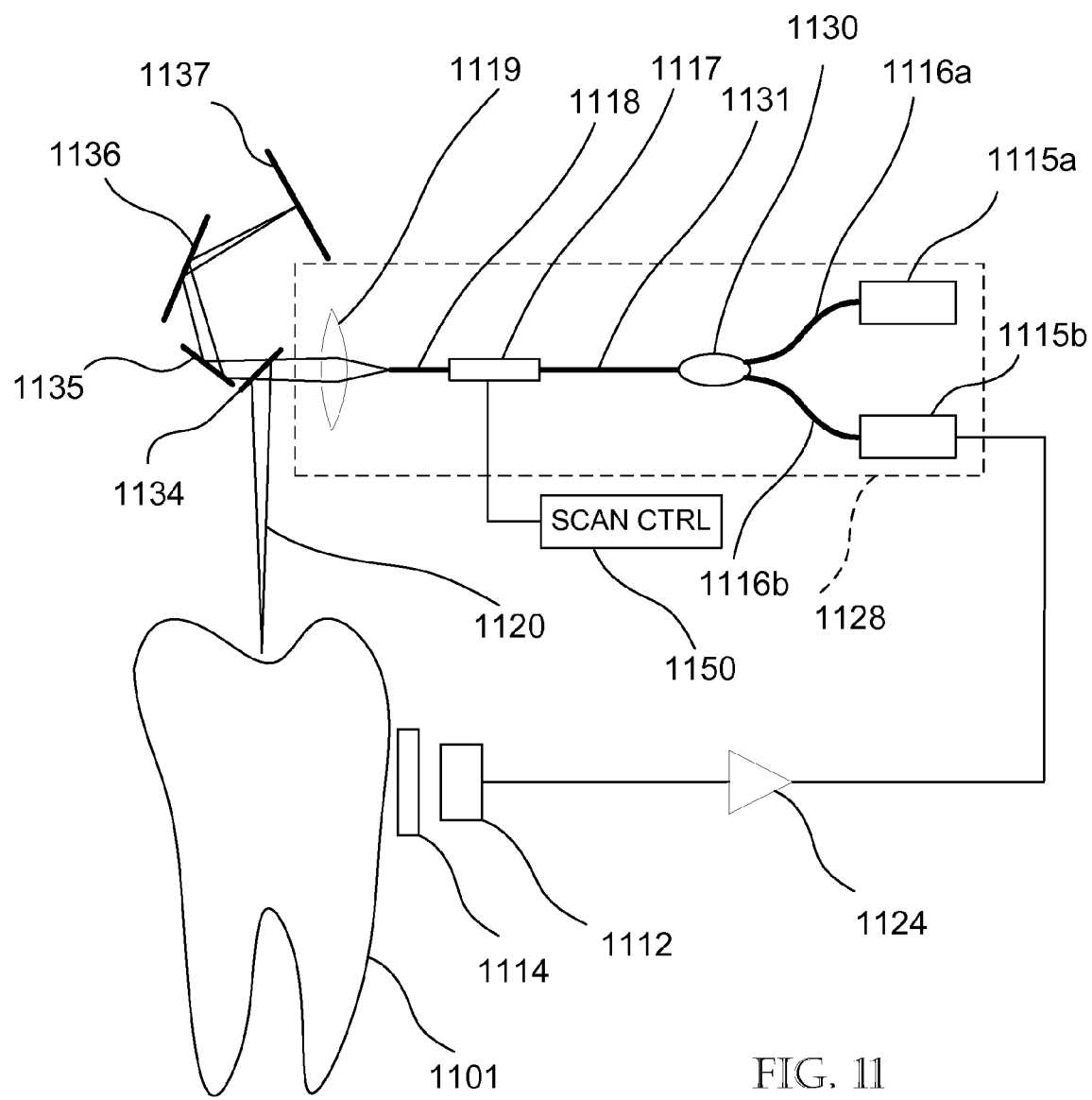
FIG. 11 is a schematic diagram of a dental imaging system that uses a common scanner for interrogation of a tooth and display of a visible image based on the interrogation.

Referring to FIG. 11, a dental imaging system includes a scanning assembly 1128 that comprises an interrogation laser 1115a and visible display laser 1115b of different wavelengths that are coupled to respective optical fibers 1116a, 1116b. A fiber coupler 1130 is coupled to the optical fibers 1116a, 1116b and combines portions of the optical fluxes from the lasers 1115a, 1115b to produce a combined flux in an optical fiber 1131. The laser 1115a provides an optical flux that can penetrate a tooth to reveal internal structure, while the laser 1115b produces visible light that can be used to provide a visible image.

A distal end 1118 of the optical fiber 1131 protrudes in cantilever fashion from a two-axis piezoelectric actuator 1117 that is driven in such a manner that the fiber end 1118 oscillates in a pre-determined two-dimensional pattern. The fiber end 1118 is imaged by a lens 1119 onto a region of the tooth 1101 or projected in a narrow beam 1120 towards the tooth 1101 after reflection by a mirror or other reflector 1134. A small motion of the fiber end 1118 can be magnified by the lens 1119 so that the pattern that is scanned by the beam at the tooth 1101 is suitably large to cover a region of interest on or in the tooth 1101. The two axes of the piezoelectric device 1117 are driven by rapid sequences of voltages from a suitable scan controller that is not shown in the drawing. For some scanning devices, including resonant fibers and resonant MEMS mirrors, the dwell time and/or density of scan lines may vary with the position of the beam, making some areas of the display brighter than others. To compensate for this, the scan controller can send a signal to the amplifier 1124 or to a multiplier stage that follows it (also not shown) in order to modulate the electronic gain between the detector 1112 and the visible laser 1115b according to the position of the scanned fiber end 1118.

The mirror 1134 is configured to reflect some portions of an incident light flux and transmit others. The mirror 1134 can be a dichroic mirror that selectively reflects an interrogation optical flux provided by the laser 1115a while transmitting a display light flux provided by the laser 1115b. In other examples, a partially transmissive mirror without wavelength sensitivity can be used, or a holographic or other reflective optical element such as a dichroic beamsplitter can be used. In other examples, the mirror 1134 can selectively reflect or transmit radiation based upon a state of polarization. Typically, the mirror 1134 is selected to reflect nearly all the light from the interrogation laser 1115a, and transmit nearly all light from the visible display laser 1115b.

Dentally modulated light from the tooth 1101 is detected by a detector 1112 after passing through a filter 1114 that rejects stray room light. The signal from the detector 1112 is amplified by an amplifier 1124 that is coupled to the visible display laser 1115b so as to modulate the intensity of the visible display laser 1115b. Visible light emerging from the fiber end 1118 passes through the mirror 1134 and is reflected by mirrors 1135, 1136, and is focused by the lens 1119 on a screen 1137, which is visible to the operator of the equipment. In the example of FIG. 11, an erect image is formed on the screen 1137. This image may be viewed in transmitted light if the screen 1137 is made of ground glass or other translucent scattering material. Because the detector 1112 and the amplifier 1124 respond quickly to the instantaneous dentally modulated light, and the intensity of the laser 1115b responds quickly to the voltage from the amplifier 1124, the instantaneous brightness of the visible spot on the screen 1137 at its current location depends on the instantaneous dentally modulated optical flux associated with the spot of interrogation light at its current location. These two geometric locations correspond nearly exactly because they are both determined by the current location of the fiber end 1118, and therefore, if the scanning is fast enough, the screen 1137 will show a picture of the tooth 1101. The amplifier 1124 may have a nonlinear response, that may be adjustable, to allow the contrast of certain features in the image to be enhanced. Many other optical configurations can be realized which embody the same principle of creating a visible image with the same scanner that is used for interrogation.

Figure 12:
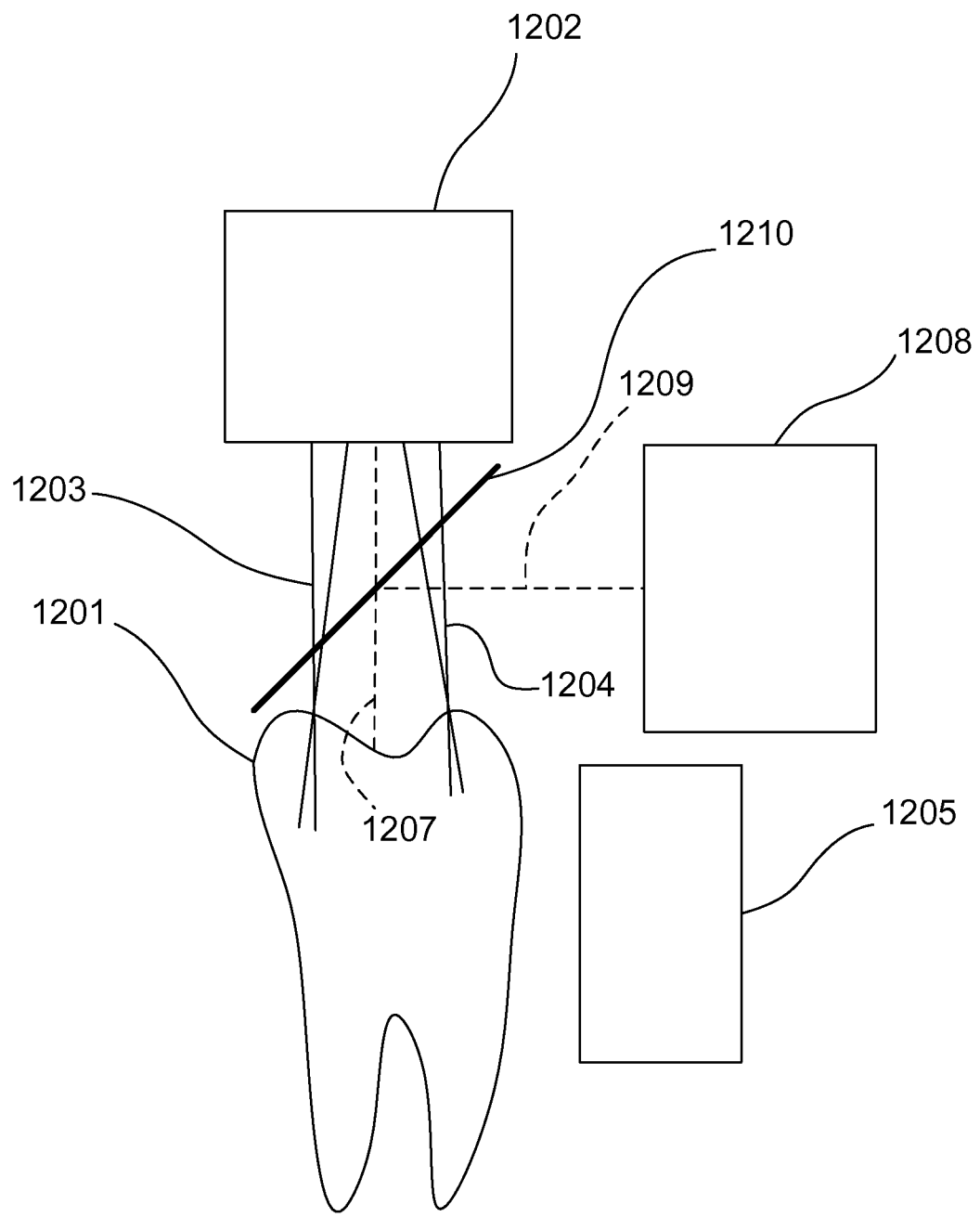
FIG. 12 is a schematic diagram of a dental imaging system that produces picture information associated with a scanned infrared interrogation beam and a visible image obtained with a camera.

FIG. 12 illustrates a scanning system 1202 that directs a scanned beam along an axis 1207 (shown as scanned to two representative locations 1203, 1204) to a tooth 1201. A dichroic mirror 1210 passes the long-wavelength light of the scanned interrogation beam, but reflects shorter-wavelength visible light. A visible light camera assembly 1208 is situated on an axis 1209 and can include, for example, a silicon array detector so as to produce an image of the tooth 1201. The dichroic mirror 1210 can be arranged so that the axis 1209 is effectively aligned with the axis 1207. Thus, the camera assembly 1208 can produce a visible light image of the tooth 1201 viewed from the direction along which the interrogation beam is incident to the tooth 1201. The camera assembly 1208 can include a short-wavelength light source that produces a short-wave illumination flux that is reflected by the mirror 1210 to illuminate the tooth 1201. With this configuration, signals from a long-wavelength detection assembly 1205 (that can include a filter for rejecting the short-wavelength illumination and other light) can be used to create a picture of the tooth in transmitted and scattered infrared light, while the camera assembly 1208 can simultaneously produce a picture of the tooth 1201 from the same angle in reflected visible light. The positions of the camera assembly 1208 and the scanning system 1202 can be adjusted, and the magnifications (whether optical or digital) can be adjusted, so that these two images are registered geometrically. The camera assembly 1208 and the scanning system 1202 can be secured by a common rigid mount that maintains the registration. In this example, a visible light image of the tooth or a portion thereof is produced by the camera assembly 1208. In other examples, the camera assembly can be arranged to produce an image of the tooth in other wavelength ranges from 400 nm to about 2000 nm.

Figure 13:
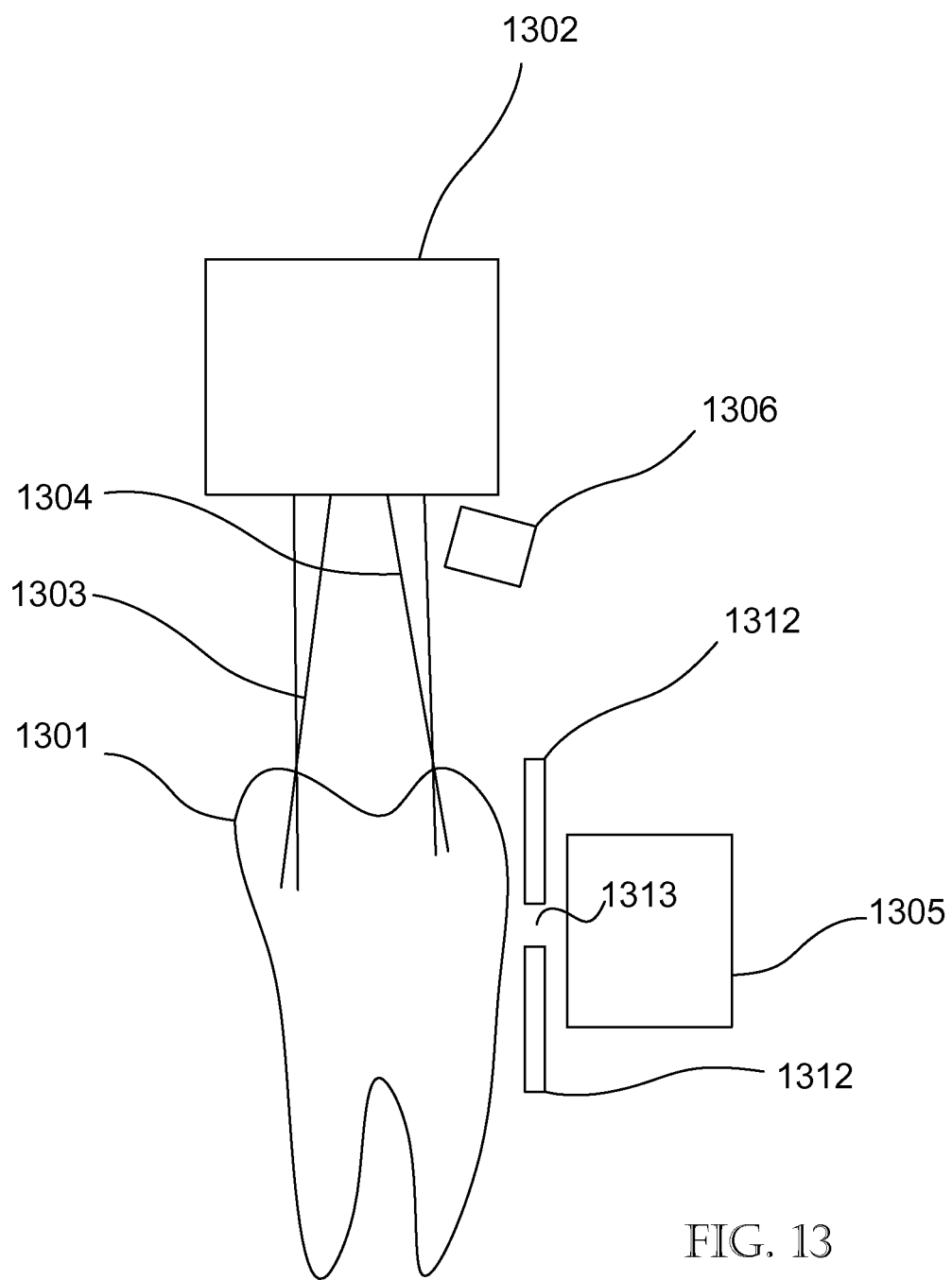
FIG. 13 is a schematic diagram of an additional exemplary dental imaging system.

FIG. 13 illustrates a scanning system 1302 that directs a scanned interrogation beam (shown as scanned to two representative locations 1303, 1304) to a biting surface of a tooth 1301. The interrogation beam can comprise two different wavelengths of light, as in the systems of FIG. 10 and FIG. 11, except that one wavelength is infrared (long wavelength) and the other is visible (short wavelength). A detector assembly 1305 is situated to detect the long-wavelength infrared light emerging from the side of the tooth, and can include a filter for rejecting short-wavelength light. A signal produced by the detector assembly 1305 can be used to create a picture of the tooth in transmitted and scattered infrared light. A detector assembly 1306 can be situated near the scanning system 1302 and selected to detect short-wavelength (visible light) that is reflected from the tooth 1301, and can include a filter for rejecting long-wavelength light. Alternatively, if the infrared light of the interrogation beam has a sufficiently long wavelength, the detector in the detection assembly 1306 can simply be made of a material such as silicon that is relatively insensitive to long-wavelength light. A filter can be conveniently provided to reject ambient short-wavelength light while permitting wavelengths associated with the visible portion of the interrogation beam to reach a detector. The portion of the scanned visible light that is detected by the detector assembly 1306 can be used to create a picture of the tooth 1301 in reflected visible light. Because both the long wavelength and short wavelength components of the interrogation beam come from the same scanner, the two pictures will automatically be registered geometrically, with no special alignment. If the top surface of the tooth 1301 has a pattern of stains such as are common in the crevasses of molars, the reflected visible image will generally show the stains as dark areas, but the infrared image will generally not show the stains if the wavelength is appropriately long, such as 1310 nm, because normal stains are invisible to this light. Instead, the infrared image can show demineralized areas of the tooth. This is useful, because the combination of the two images will show the locations of the demineralization in relation to the stains.

FIG. 13 also shows a mask 1312 that defines an aperture 1313. In the example of FIG. 13, the aperture is a slit that extends horizontally (i.e., perpendicular to the plane of the drawing). The mask 1312 is made from an opaque material that is penetrated by the aperture 1313 (for example, by a horizontal slit), and it is situated to restrict the detector 1305 from receiving light fluxes except those that exit the tooth 1301 from a horizontal stripe corresponding to the aperture 1313. The pictures that this system creates will be similar to pictures created by a camera or array looking at the top of a tooth while a horizontal stripe along its side is illuminated with infrared light. It has been found that this arrangement often produces a better picture than illuminating the whole side of the tooth. For purposes of this disclosure, the mask 1312 with the aperture 1313 comprises a light coupling device, even though it controls the coupled light by restriction rather than addition of light flux. A more sophisticated design that includes reflection or refraction (such as a light conduit or a lens) can be used to couple more light to the detector than a mere slit, by capturing high-angle rays that would otherwise miss the detector, while still confining the spatial coupling to a stripe on the side of the tooth.

In some example systems, a second optical scanning system (a display optical scanning system) can be provided to form an image associated with a dentally modulated optical flux. Such an image can be conveniently formed on an image surface situated in proximity to the tooth or teeth under investigation so that the dental practitioner can continue to inspect the tooth or teeth while viewing a scanned image based on infrared scan data. The display optical scanner can use one or more visible display beams (for example, each wavelength of one or more multi-wavelength scans can be displayed in a unique color; or combinations of wavelengths can be used to create false colors that highlight variations that might be too subtle in a gray-scale display). In addition, the visible display beams can be modulated to produce the displayed image based on a current dental scan or based on picture information from one or more previous scans. The display optical system can use the same scanning system used to scan the interrogation beam so that the displayed image can be readily arranged in alignment with corresponding features of the tooth. With such systems, external imaging devices and processors (including computers) are unnecessary, and such systems can be especially compact and inexpensive. Such systems can also exhibit low power consumption, and are suitable for use in remote field locations as well as in a sophisticated dental office.

The example dental imaging systems described above are based on scanning an optical interrogation beam having a wavelength that penetrates a tooth so that picture information or images of a tooth interior can be obtained. However, in some applications, an infrared camera can be used, and portions of a tooth imaged directly. In direct imaging systems, an optical correction system as described above can be situated so as to reduce image artifacts associated with a refractive index difference between a tooth and air. The partial index-matching provided with an optical correction device tends to diminish the contributions of surface irregularities and permits internal features of a tooth to be imaged with higher accuracy. Camera-based images can also be obtained at different wavelengths by, for example, illuminating a tooth with light sources of two different wavelengths and obtaining corresponding images, or illuminating with a relatively broad spectrum source and selecting wavelength ranges for imaging using one or more optical filters. Camera-based images can also be obtained from different positions by moving the camera or using a mirror to obtain different views of a tooth.

Light coupling devices situated to direct or couple light fluxes to or from a tooth are generally situated at or near a tooth in a subject's mouth. Therefore, disposable light coupling devices can be convenient. In this way, sterilization or other cleaning procedures for such devices are unnecessary. Optical devices that direct or focus the input beam in a scanning device, or that direct or focus light to a camera device, can also be made as disposable light coupling devices. A device situated at or near a tooth in a subject's mouth that is attached to an assembly that includes a scanner or camera can act as a spacer to hold the scanner or camera at the proper distance from the tooth and/or it can act to steady the scanner or camera, as might be desired for good focus or other requirements, and such a device can also be disposable. A device that keeps the scanner assembly and/or a detector assembly clean by covering all or part so that it does not contact the mouth can be disposable. In a camera-based system, a device that keeps the camera assembly and/or optical source assembly clean by covering all or part so that it does not contact the mouth can be disposable. Any combination of the functions of light coupling, directing, focusing, distancing, positioning, steadying and sanitary protection can be combined in a single device, and such a device can also be disposable.

In view of the many possible embodiments to which the principles of the disclosed technology may be applied, it should be recognized that the illustrated embodiments are only preferred examples and should not be taken as limiting the scope of the technology. I claim all that is encompassed by the appended claims.

I claim:

1. A dental imaging system, comprising:
    an interrogation optical scanner configured to scan an optical interrogation beam across at least a portion of a tooth by varying positions at which the optical interrogation beam strikes a surface of the tooth, wherein the optical interrogation beam is substantially transmissible into the tooth so as to produce a dentally modulated optical flux exiting the interior of the tooth;
    an optical detection system that includes at least one photodetector situated to receive diffuse light associated with the dentally modulated optical flux from an exit surface area of the tooth along a plurality of directions that are not co-linear with the optical interrogation beam, wherein the at least one photodetector is configured to remain substantially fixedly optically coupled to the exit surface area of the tooth during the scan of the optical interrogation beam, the optical detection system configured to produce at least one direct detection signal associated with the diffuse light received from the tooth; and
    a signal processor coupled to receive the at least one direct detection signal and produce picture information associated with the tooth based on the at least one direct detection signal and position information derived from the positions of the optical interrogation beam.

2. The dental imaging system of claim 1, further comprising an optical-correction device situated to receive the scanned interrogation beam and direct the scanned interrogation beam into the tooth.

3. The dental imaging system of claim 2, wherein the optical-correction device includes an exit surface that is conformable to the surface of the tooth.

4. The dental imaging system of claim 2, wherein the optical-correction device has a refractive index corresponding to a refractive index of the tooth.

5. The dental imaging system of claim 2, wherein the optical-correction device comprises a gel.

6. The dental imaging system of claim 2 wherein the optical-correction device comprises a flexible solid material.

7. The dental imaging system of claim 1, further comprising a light-coupling device situated to direct the received diffuse light to the at least one photodetector.

8. The dental imaging system of claim 7, wherein the light-coupling device comprises a fluid or a gel.

9. The dental imaging system of claim 7, wherein the light-coupling device has a refractive index corresponding to a refractive index of the tooth.

10. The dental imaging system of claim 7, wherein the at least one photodetector is situated and configured so as to be spaced away from the tooth by the light-coupling device.

11. The dental imaging system of claim 7 wherein the light-coupling device comprises a flexible solid material.

12. The dental imaging system of claim 7, wherein the light-coupling device covers at least a portion of the interrogation optical scanner or the optical detection system.

13. The dental imaging system of claim 7, wherein the coupling device is disposable.

14. The dental imaging system of claim 1, further comprising a coupling device that directs the optical interrogation beam to the tooth.

15. The dental imaging system of claim 14, wherein the coupling device is disposable.

16. The dental imaging system of claim 1, further comprising a laser diode that is situated to produce the optical interrogation beam and direct the optical interrogation beam to the interrogation optical scanner.

17. The dental imaging system of claim 1, further comprising an optical filter situated with respect to the optical detection system so as to preferentially reject light fluxes in wavelength ranges that are different from a wavelength range associated with the dentally modulated optical flux.

18. The dental imaging system of claim 1, wherein the at least one photodetector of the optical detection system comprises a first photodetector and a second photodetector configured to remain substantially fixedly optically coupled to the exit surface area during the scan of the optical interrogation beam and that are configured so as that the at least one direct detection signal includes a first direct detection signal and a second direct detection signal, respectively, associated with the diffuse light received from the tooth, and the signal processor is coupled to receive the first and second direct detection signals and produce picture information associated with the tooth based on the first and second direct detection signals and position information derived from the positions of the optical interrogation beam.

19. The dental imaging system of claim 18, wherein the optical interrogation beam includes an optical flux in a first wavelength range and an optical flux in a second wavelength range, and the first photodetector and the second photodetector produce the first direct detection signal and the second direct detection signal based on a dentally modulated optical flux in the first wavelength range and the second wavelength range, respectively.

20. A method, comprising:
scanning an interrogation optical beam across at least a portion of a tooth by varying positions at which the optical interrogation beam strikes a surface of the tooth, wherein the optical interrogation beam is substantially transmissible into the tooth, so as to produce a dentally modulated optical flux exiting the interior of the tooth;
receiving diffuse light associated with the dentally modulated optical flux from an exit surface area of the tooth along a plurality of directions that are not co-linear with the optical interrogation beam with a photodetector that is fixedly optically coupled to the exit surface area during the scanning of the optical interrogation beam; and
producing picture information associated with the tooth based on the received diffuse light and the varying positions at which the optical interrogation beam strikes the surface of the tooth.

21. The method of claim 20, wherein the diffuse light is received at a first detector location and a second detector location, wherein the first and second detector locations are fixed with respect to the tooth, and the picture information is produced based on diffused light received at the first and second detector locations.

22. The method of claim 21, wherein the optical interrogation beam includes an optical flux in a first wavelength range and an optical flux in a second wavelength range, and the received diffuse light contains portions of the optical flux in the first wavelength range and the second wavelength range, and the picture information is produced based on the portions of the optical flux in the first wavelength range and the second wavelength range.

* * * * *